United States Patent [19]

Masamune

[11] Patent Number: 5,502,072
[45] Date of Patent: Mar. 26, 1996

[54] SUBSTITUTED OXINDOLES

[75] Inventor: Hiroko Masamune, Noank, Conn.

[73] Assignee: Pfizer Inc., New York, N.Y.

[21] Appl. No.: 164,973

[22] Filed: Nov. 26, 1993

[51] Int. Cl.⁶ .................... A61K 31/40; C07D 209/12
[52] U.S. Cl. .................... 514/418; 514/300; 546/113; 548/486
[58] Field of Search .................... 548/486; 514/418, 514/300; 546/113

[56] References Cited

U.S. PATENT DOCUMENTS

| | | | |
|---|---|---|---|
| 4,582,834 | 4/1986 | Stenzel | 514/274 |
| 4,971,959 | 11/1990 | Hawkins | 514/150 |
| 5,077,290 | 12/1991 | Fisher et al. | 514/233.2 |

FOREIGN PATENT DOCUMENTS

| | | | |
|---|---|---|---|
| 0247725A2 | 12/1987 | European Pat. Off. | |
| 0303418A2 | 2/1989 | European Pat. Off. | |
| 0428313A2 | 5/1991 | European Pat. Off. | |
| 0442204A2 | 8/1991 | European Pat. Off. | |
| 0470805A1 | 2/1992 | European Pat. Off. | |
| 0473963 | 3/1992 | European Pat. Off. | |
| 0497564A1 | 8/1992 | European Pat. Off. | |
| 0511865A1 | 11/1992 | European Pat. Off. | |
| 3742716A1 | 6/1989 | Germany. | |
| 4027592A1 | 3/1992 | Germany. | |
| 8706576 | 11/1987 | WIPO. | |
| 9107178 | 5/1991 | WIPO. | |
| 9115451 | 10/1991 | WIPO. | |
| 9116303 | 10/1991 | WIPO. | |
| 9200968 | 1/1992 | WIPO. | |
| 9207567 | 5/1992 | WIPO. | |
| 92007830 | 5/1992 | WIPO | 548/486 |
| 9212961 | 8/1992 | WIPO. | |

OTHER PUBLICATIONS

Sainsbury, M. "Electrochemical Oxidation of Aromatic Ethers" *J.C.S. Perkin I*, 1979, pp. 108–114.

Lal, B., "Novel Diuretic Agents" *Indian Journal of Chemistry* vol. 13, Sep. 1975, pp. 898–903.

Lal, B. et al., CA:84:121,586p. Apr., 1976.

Beavo et al., "Primary Sequence of Cyclic Nucleotide Phosphodiesterase Isozymes and the Design of Selective Inhibitors," *TIPS*, 1990, 11, 150.

Nicholson et al., "Differential Modulation of Tissue Function and Therapeutic Potential of Selective Inhibitors of Cyclic Nucleotide Phosphodiesterase Isoenzymes," *TIPS*, 1991, 12, 19.

O'Donnell et al., "Directions for New Anti–Asthma Drugs," T. J. Torphy, 37, 1988, Birkhauser–Verlag.

Sutherland et al., "The Relation of Adenosine–3',5'–Phosphate and Phosphorylase to the Actions of Catecholamines and Other Hormones," *Pharmacol. Rev.*, 12, 1960, pp. 265–299; and.

Verghese et al., "Anti–Neutophil Activity of Cyclic Nucleotide Phosphodiesterase Inhibitors With Varying Cardiotonic Potencies," *J. Mol. Cell Cardiol.*, 12, (Supp. II), S.61, 1989.

*Primary Examiner*—Jacqueline Haley
*Attorney, Agent, or Firm*—Peter C. Richardson; Gezina Holtrust; B. Timothy Creagan

[57] ABSTRACT

The present invention relates to novel substituted oxindoles of the formula I as defined below and related compounds, pharmaceutical compositions comprising such compounds, and the use of such compounds as inhibitors of phosphodiesterase ("PDE") type IV. The compounds of this invention are useful in the treatment of AIDS, asthma, rheumatoid arthritis, osteoarthritis, bronchitis, chronic obstructive airways disease, psoriasis, allergic rhinitis, atopic, dermatitis, shock, other inflammatory diseases, and other conditions where the action of phosphodiesterase type IV is implicated.

9 Claims, No Drawings

SUBSTITUTED OXINDOLES

BACKGROUND OF THE INVENTION

The present invention relates to novel substituted oxindoles and related compounds, pharmaceutical compositions comprising such compounds, and the use of such compounds as inhibitors of phosphodiesterase ("PDE") type IV. The compounds of this invention are useful in the treatment of AIDS, asthma, rheumatoid arthritis, osteoarthritis, bronchitis, chronic obstructive airways disease, psoriasis, allergic rhinitis, atopic dermatitis, shock, and other inflammatory diseases. This invention also relates to pharmaceutical compositions containing these compounds and to methods of inhibiting the action of phosphodiesterase type IV.

Since the recognition that cyclic adenosine monophosphate ("cAMP") is an intracellular second messenger (E. W. Sutherland and T. W. Rall, *Pharmacol. Rev.*, 1960, 12, 265), inhibition of phosphodiesterases has been a target for modulation and, accordingly, therapeutic intervention in a range of disease processes. Distinct classes of phosphodiesterases have been recognized (J. A. Beavo and D. H. Reifsnyder, *TIPS*, 1990, 11, 150) and their selective inhibition has led to improved drug therapies (C. D. Nicholson, R. A. Challiss, and M. Shahid, *TIPS*, 1991, 12, 19). It has been claimed that inhibition of PDE type IV can lead to inhibition of inflammatory mediator release (M. W. Verghese, et al., *J. Mol. Cell Cardiol.*, 1989, 12 (Supp. II), S 61) and airway smooth muscle relaxation (T. J. Torphy in *Directions for New Anti-Asthma Drugs*, eds. S. R. O'Donnell and C. G. A. Persson, 1988, 37, Birkhauser-Verlag).

Certain pyrimidone compounds have been described as antidepressants in EP 0 247 725 A2, published Dec. 2, 1987. Certain pyrimidone compounds have been described as useful against asthma and certain skin disorders in WO 91/07178 published May 30, 1991.

The following documents relate to inhibitors of phosphodiesterase type IV: WO 87/06576, published Nov. 5, 1987; WO 91/15451, published Oct. 17, 1991; WO 91/16303, published Oct. 31, 1991; WO 92/00968, published Jan. 23, 1992; WO 92/07567, published May 14, 1992; WO 92/12961, published Aug. 6, 1992; EP 0 428 313 A2, published May 22, 1991; EP 0 442 204 A2, published Aug. 21, 1991; EP 0 470 805 A1, published Feb. 12, 1992; EP 0 473 963 A1, published Mar. 11, 1992; EP 0 497 564 A1, published Aug. 5, 1992; EP 0 511 865 A1, published Nov. 4, 1992; and EP 0 303 418 A2, published Feb. 15, 1989. The following documents relate to inhibitors of phosphodiesterase type IV in non-pulmonary/nonallergic uses: U.S. Pat. No. 4,582,834, issued Apr. 15, 1986; U.S. Pat. No. 4,971,959, issued Nov. 20, 1990; U.S. Pat. No. 5,077,290, issued Dec. 31, 1991; DE 3742716 A1, published Jun. 22, 1989; and DE 4027592 A1, published Mar. 5, 1992.

All documents cited herein, including the foregoing, are incorporated herein by reference in their entireties.

SUMMARY OF THE INVENTION

The present invention relates to a compound of the formula:

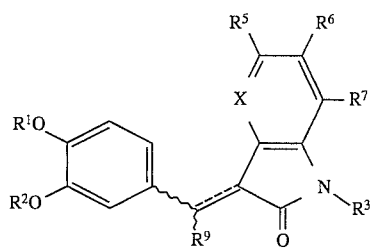

wherein X is N or $CR^4$;

$R^1$ is $(C_1-C_4)$alkyl or phenyl-$(C_1-C_6)$alkyl;

$R^2$ is $(C_1-C_{10})$alkyl, phenyl-$(C_1-C_6)$alkyl, $(C_3-C_7)$ cycloalkyl, or $(C_6-C_{12})$ polycycloalkyl;

or $R^1$ and $R^2$, taken together with the oxygens to which they are attached, represent a methylene or ethylene bridge which forms a 5 or 6 membered ring;

$R^3$ is hydrogen, $(C_1-C_6)$alkyl, $(C_1-C_6)$alkyloxycarbonyl, $(C_1-C_6)$alkyloxy, $(C_{1-C_6})$ alkoxycarbonyl-$(C_1-C_6)$alkyl, $—CONR^{10}R^{11}$; or $—(C_1-C_6)$alkyl-$CONR^{10}R^{11}$;

$R^{10}$ and $R^{11}$ are independently selected from hydrogen and $(C_1-C_6)$alkyl, or $R^{10}$ and $R^{11}$, taken together with the nitrogen to which they are attached, form a pyrrolidine or piperidine ring;

$R^4$, $R^5$, $R^6$ and $R^7$ are independently selected from hydrogen, halogen, $(C_1-C_8)$ alkoxy, $(C_3-C_7)$ cycloalkyloxy, hydroxy, $(C_2-C_6)$ acyloxy, nitro, $NR^8R^{12}$, $SO_2NR^8R^{12}$, $(C_1-C_6)$alkyl, $(C_1-C_6)$alkylcarbonyl, phenyl-$(C_1-C_6)$alkoxy, and $(C_6-C_{12})$ polycycloalkoxy or any combination of $R^4$ and $R^5$, $R^5$ and $R^6$, or $R^6$ and $R^7$ which together form $—OCH_2O—$ or $—OCH_2CH_2O—$, such that, when taken together with the carbons to which they are attached, they form, respectively, a 5- or 6-membered ring;

$R^8$ and $R^{12}$ are independently selected from hydrogen and $(C_1-C_6)$alkyl, or $R^8$ and $R^{12}$, taken together with the nitrogen to which they are attached, form a pyrrolidine or piperdine ring;

$R^9$ is hydrogen or $(C_1-C_6)$alkyl;

the broken line represents an optional double bond; and the wavy lines indicate that the compounds exist as (E) and/or (Z) stereoisomers when the broken line is a double bond;

with the proviso that (a) if $R^1$ and $R^2$ are both methyl, X is CH, $R^9$ is hydrogen, and the broken line is a double bond, then (i) at least one of $R^3$, $R^5$, $R^6$, and $R^7$ is other than hydrogen; (ii) at least one of $R^5$, $R^6$ and $R^7$ is other than hydrogen or $R^3$ is other than methyl; and (iii) at least one of $R^3$ and $R^7$ is other than hydrogen or at least one of $R^5$ and $R^6$ is other than $O—CH_3$; (b) if $R^3$ is hydrogen, $R^9$ is hydrogen, X is CH, the broken line is a double bond, and $R^1$ and $R^2$ together represent a methylene bridge, then at least one of $R^5$, $R^6$ and $R^7$ is other than hydrogen; and (c) if $R^1$ and $R^2$ are both methyl, X is CH, $R^9$ is hydrogen, and the broken line is a single bond, then at least one of $R^5$ and $R^6$ is other than $O—CH_3$, or $R^7$ is other than hydrogen, or $R^3$ is other than $COCH_3$;

or a pharmaceutically acceptable salt thereof.

The terms "halo" or "halogen", as used herein, unless otherwise indicated, includes chloro, fluoro, bromo and iodo.

The term "alkyl", as used herein, unless otherwise indicated, includes saturated monovalent hydrocarbon radicals having straight or branched moieties, for example, methyl, ethyl, n-propyl, isopropyl and t-butyl.

The term "cycloakyl," unless otherwise indicated, means a saturated carbocyclic radical, for example, cyclopropyl, cyclobutyl, cyclopentyl or cyclohexyl.

The term "alkoxy", unless otherwise indicated, includes O-alkyl groups wherein "alkyl" is defined as above.

The term "polycycloalkyl" means a saturated carbopolycyclic radical, such as norbornyl, bicyclo[2.2.2]octyl, or adamantyl.

The term "alkyloxycarbonyl" means an alkoxy group (as defined above) attached to a carbonyl moiety.

The term "alkyloxy" means the same as alkoxy.

The term "cycloalkyloxy" includes O-cycloalkyl groups wherein cycloalkyl is defined as above.

The term "acyloxy" means an alkyl group (as defined above) attached to a carbonyl moiety which is then attached to an oxygen.

The term "alkylcarbonyl" means an alkyl group (defined as above) attached to a carbonyl moiety.

A preferred compound of the present invention is a compound of the formula I wherein $R^1$ is methyl or ethyl and $R^2$ is $(C_1-C_6)$alkyl, phenyl-$(C_1-C_6)$alkyl, $(C_3-C_7)$ cycloalkyl, or $(C_6-C_{12})$ polycycloalkyl; or $R^1$ and $R^2$, taken together with the oxygens to which they are attached, represent a methylene or ethylene bridge which forms a 5 or 6 membered ring.

In a more preferred embodiment, X is CH or N, $R^1$ is methyl, $R^2$ is norbornyl, $R^3$ is hydrogen, methyl, ethyl, —$COOC_2H_5$, —$CONH_2$, methoxy or —$CH_2COOC_2H_5$, $R^6$ is hydrogen, bromo, methoxy or chloro, and $R^5$ is hydrogen, hydroxy, cyclopentyloxy, methoxy, bromo, chloro, amino, or —$SO_2NH_2$, or $R^5$ and $R^6$ together form —$OCH_2O$—, $R^7$ is hydrogen, and $R^9$ is hydrogen or methyl.

Specific preferred compounds of the present invention are:

3-[[3-(Bicyclo[2.2.1]hept-2-yloxy)-4-methoxyphenyl]methylene]-1,3-dihydro-[1α,2α(E),4α]-2H-indol-2-one;

3-[[3-(Bicyclo[2.2.1]hept-2-yloxy)-4-methoxyphenyl]methylene]-1,3-dihydro-1-ethyl-[1α,2α(E),4α]-2H-indol-2-one;

3-[[3-(Bicyclo[2.2.1]hept-2-yloxy)-4-methoxyphenyl]methylene]-1,3-dihydro-1-methyl-[1α,2α(Z),4α]-2H-indol-2-one;

3-[[3-(Bicyclo[2.2.1]hept-2-yloxy)-4-methoxyphenyl]methylene]-1,3-dihydro-1-ethyl-[1α,2α(Z),4α]-2H-indol-2-one;

3-[[3-(Bicyclo[2.2.1]hept-2-yloxy)-4-methoxyphenyl]methylene]-6-chloro-1,3-dihydro-1-methoxy-[1α,2α(Z),4α]-2H-indol-2-one;

3-[[3-(Bicyclo[2.2.1]hept-2-yloxy)-4-methoxyphenyl]methylene]-6-chloro-1,3-dihydro-[1α,2α(E),4α]-2H-indol-2-one;

3-[[3-(Bicyclo[2.2.1]hept-2-yloxy)-4-methoxyphenyl]methylene]-5-bromo-1,3-dihydro-[1α,2α(E),4α]-2H-indol-2-one;

3-[[3-(Bicyclo[2.2.1]hept-2-yloxy)-4-methoxyphenyl]methylene]-5-bromo-1,3 -dihydro-1-methyl-[1α,2α(E),4α]-2H-indol-2-one;

3-[[3-(Bicyclo[2.2.1]hept-2-yloxy)-4-methoxyphenyl]methylene]-5-chloro-1,3-dihydro-1-methyl-[1α,2α(Z),4α]-2H-indol-2-one;

3-[[3-(Bicyclo[2.2.1]hept-2-yloxy)-4-methoxyphenyl]methylene ]-5-cyclopentyloxy-1,3-dihydro-1-ethyl-[1α,260 (E),4α]-2H-indol-2-one;

3-[[3-(Bicyclo[2.2.1]hept-2-yloxy)-4-methoxyphenyl]methylene]-6-methoxy-1,3 -dihydro-1-methyl-[1α,2α(E),4α]-2H-indol-2-one; and 3-[[3-(Bicyclo[2.2.1]hept-2-yloxy)-4-methoxyphenyl]methylene]-2,3-dihydro-N,N-dimethyl-2-oxo-[1α,2α(E),4α]-1H-indole-5-sulfonamide.

Other compounds of the present invention include the following:

3-[[3-(Bicyclo[2.2.1]hept-2-yloxy)-4-methoxyphenyl]methylene]-1,3-dihydro-[1α,2α(Z),4α]-2 H-indol-2-one;

3-[[3-(Bicyclo[2.2.1]hept-2-yloxy)-4-methoxyphenyl]methyl]-1,3-dihydro-2H-indol-2-one;

3-[[3-(Bicyclo[2.2.1]hept-2-yloxy)-4-methoxyphenyl]methylene]-5-hydroxy-1,3 -dihydro-1α,2α(Z),4α]-2H-indol-2-one;

3-[[3-(Bicyclo[2.2.1]hept-2-yloxy)-4-methoxyphenyl]methylene]-5-hydroxy-1,3 -dihydro-[1α,2α(E),4α]-2H-indol-2-one;

3-[[3-(Bicyclo[2.2.1]hept-2-yloxy)-4-methoxyphenyl]methyl]-5-hydroxy-1,3-dihydro-2H-indol-2-one;

3-[[3-(Bicyclo[2.2.1]hept-2 -yloxy)-4-methoxyphenyl]methylene]-2,3-dihydro-2-oxo-[1α,2α(E),4α]-1H-indole-1-carboxylic acid, ethyl ester;

3-[[3-(Bicyclo[2.2.1]hept-2-yloxy)-4-methoxyphenyl]methylene]-1,3-dihydro-1-methyl-[1α,2α(E),4α]-2H-indol-2-one;

3-[[3-(Bicyclo[2.2.1]hept-2-yloxy)-4-methoxyphenyl]methylene]-2,3-dihydro-2-oxo-[1α,2α(Z),4α]-1H-indol-1-carboxylic acid, ethyl ester;

5-Acetyloxy-3-[[3-(bicyclo[2.2.1]hept-2-yloxy)-4-methoxyphenyl]methylene]-1,3 -dihydro-[1α,2α(Z),4α]-2H-indol-2-one;

3-[[3-(Bicyclo[2.2.1]hept-2-yloxy)-4-methoxyphenyl]methylene]-6-chloro-1,3-dihydro-1-methoxy-[1α,2α(E),4α]-2H-indol-2-one;

3-[[3-(Bicyclo[2.2.1]hept-2-yloxy)-4-methoxyphenyl]methylene]-5-cyclopentyloxy-1,3-dihydro-[1α,2α(E),4α]-2H-indol-2-one;

3-[[3-(Bicyclo[2.2.1]hept-2-yloxy)-4-methoxyphenyl]methylene]-5-cyclopentyloxy-1,3-dihydro-[1α,2α(Z),4α]-2H-indol-2-one;

3-[[3-(Bicyclo[2.2.1]hept-2-yloxy)-4-methoxyphenyl]methylene]-6-chloro-1,3 -dihydro-[1α,2α(Z),4α]-2H-indol-2-one;

(Z)-3-[(2,3-Dihydro-1,4-benzodioxin-6-yl)methylene]-1,3-dihydro-2H-indol-2-one;

3-[(3,4-Dimethoxyphenyl)methylene]-1,3-dihydro-[1α,2α(E),4α]-2H-indol-2-one;

(E)-3-[(2,3-Dihydro-1,4-benzodioxin-6-yl)methylene]-1,3-dihydro-2H-indol-2-one;

(E)-3-(1,3-Benzodioxol-5-ylmethylene)-1,3-dihydro-2H-indol-2-one;

3-[[3-(Bicyclo[2.2.1]hept-2-yloxy)-4-methoxyphenyl]methylene]-5-bromo-1,3-dihydro-[1α,2α(Z),4α]-2H-indol-2-one;

3-[[3-(Bicyclo[2.2.1]hept-2-ylo xy)-4-methoxyphenyl]methylene]-5-cyclopentyloxy-1,3-dihydro-1-methyl-[1α,2α(Z),4α]-2H-indol-2-one;

3-[[3-(Bicyclo[2.2.1]hept-2-yloxy)-4-methoxyphenyl]methylene]-5-bromo-1,3-dihydro-1-methyl-[1α,2α(Z),4α]-2H-indol-2-one;

3-[[3-(Bicyclo[2.2.1]hept-2-yloxy)-4-methoxyphenyl]methylene]-5-chloro-1,3 -dihydro[1α,2α(E),4α]-2H-pyrrolo [3,2-b]pyridin-2-one;

(E)-1,3-Dihydro-3-[[4-methoxy-3-(4-phenylbutoxy)phenyl]-methylene]-2H-indol-2-one;

3-[[3-(Bicyclo[2.2.1]hept-2-yloxy)-4-methoxyphenyl]methylene ]-5-chloro-1,3 -dihydro-1-methyl-[1α,2α(E),4α]-2H-indol-2-one;

3-[[3-(Bicyclo[2.2.1]hept-2-yloxy)-4-methoxyphenyl]methylene]-5-chloro-1,3-dihydro-1-methyl-[1α,2α(E),4α]-2H-pyrrolo[3,2-b]pyridin-2-one;

3-[[3-(Bicyclo[2.2.1]hept-2-yloxy)-4-methoxyphenyl]methylene]-5,7-dinitro-1,3-dihydro-[1α,2α(E),4α]-2H-indol-2-one;

3-[[3-(Bicyclo[2.2.1]hept-2-yloxy)-4-methoxyphenyl]methylene]-5-nitro-1,3-dihydro-[1α,2α(E),4α]-2H-indol-2-one;

3-[[3-(Bicyclo[2.2.1]hept-2-yloxy)-4-methoxyphenyl]methylene]-5-nitro-1,3-dihydro-[1α,2α(Z),4α]-2H-indol-2-one;

3-[[3-(Bicyclo[2.2.1]hept-2-yloxy)-4-methoxyphenyl]methylene]-5,6-dimethoxy-1,3-dihydro-1-methyl-[1α,2α(E),4α]-2H-indol-2-one;

3-[[3-(Bicyclo[2.2.1]hept-2-yloxy)-4-methoxyphenyl]methylene]-5,6-dimethoxy-1,3-dihydro-1-methyl-[1α,2α(Z),4α]-2H-indol-2-one;

3-[[3-(Bicyclo[2.2.1]hept-2-yloxy)-4-methoxyphenyl]methylene]-5-nitro-1,3-dihydro-1-methyl-[1α,2α(E),4α]-2H-indol-2-one;

3-[[3-(Bicyclo[2.2.1]hept-2-yloxy)-4-methoxyphenyl]methylene]-5-hydroxy-1,3-dihydro-1-ethyl-[1α,2α(Z),4α]-2H-indol-2-one;

3-[[3-(Bicyclo[2.2.1]hept-2-yloxy)-4-methoxyphenyl]methylene]-5,7-dinitro-1,3-dihydro-1-methyl-[1α,2α(E),4α]-2H-indol-2-one;

5-Amino-3-[[3-(bicyclo[2.2.1]hept-2-yloxy)-4-methoxyphenyl]methyl]-1,3-dihydro-1-methyl-2H-indol-2-one;

3-[[3-(Bicyclo[2.2.1]hept-2-yloxy)-4-methoxyphenyl]methylene]-5-cyclopentyloxy-1,3-dihydro-1-ethyl-[1α,2α(Z),4α]-2H-indol-2-one;

5-Amino-3-[[3-(bicyclo[2.2.1]hept-2-yloxy)-4-methoxyphenyl]methylene]-1,3-dihydro-1-methyl-[1α,2α(Z),4α]-2H-indol-2-one;

3-[[3-(Bicyclo[2.2.1]hept-2-yloxy)-4-methoxyphenyl]methylene]-1,3-dihydro-[1α,2α(E),4α]-2H-pyrrolo[3,2-b]pyridin-2-one;

3-[[3-(Bicyclo[2.2.1]hept-2-yloxy)-4-methoxyphenyl]methylene]-6-methoxy-1,3-dihydro-[1α,2α(Z),4α]-2H-indol-2-one;

3-[[3-(Bicyclo[2.2.1]hept-2-yloxy)-4-methoxyphenyl]methylene]-5-methoxy-1,3-dihydro-1-methyl-[1α,2α(E),4α]-2H-indol-2-one;

3-[[3-(Bicyclo[2.2.1]hept-2-yloxy)-4-methoxyphenyl]methylene]-5-methoxy-1,3-dihydro-1-methyl-[1α,2α(Z),4α]-2H-indol-2-one;

3-[[3-(Bicyclo[2.2.1]hept-2-yloxy)-4-methoxyphenyl]methylene]-6-methoxy-1,3-dihydro-1-methyl-[1α,2α(Z),4α]-2H-indol-2-one;

3-[[3-(Bicyclo[2.2.1]hept-2-yloxy)-4-methoxyphenyl]methylene]-1,3-dihydro-1-methyl-[1α,2α(E),4α]-2H-pyrrolo[3,2-b]pyridin-2-one;

3-[[3-(Bicyclo[2.2.1]hept-2-yloxy)-4-methoxyphenyl]methylene]-5-chloro-2,3-dihydro-2-oxo-[1α,2α(E),4α]-1H-indole-1-carboxamide;

3-[[3-(Bicyclo[2.2.1]hept-2-yloxy)-4-methoxyphenyl]methylene]-5-chloro-2,3-dihydro-2-oxo-[1α,2α(Z),4α]-1H-indole-1-carboxamide;

3-[[3-(Bicyclo[2.2.1]hept-2-yloxy)-4-methoxyphenyl]methylene]-5-nitro-1,3-dihydro-1-methyl-[1α,2α(E),4α]-2H-indol-2-one;

5-Acetyl-3-[[3-(bicyclo[2.2.1]hept-2-yloxy)-4-methoxyphenyl]methylene]-1,3-dihydro-[1α,2α(E),4α]-2H-indol-2-one;

5-Acetyl-3-[[3-(bicyclo[2.2.1]hept-2-yloxy)-4-methoxyphenyl]methylene]-1,3-dihyro-[1α,2α(Z),4α]-2H-indol-2-one;

(E)-3-[(3,4-Dimethoxyphenyl)methylene]-2,3-dihydro-2-oxo-1H-indole-1-acetic acid, ethyl ester;

(Z)-3-[(3,4-Dimethoxyphenyl)methylene]-2,3-dihydro-2-oxo-1H-indole-1-acetic acid, ethyl ester;

(E)-5-Bromo-3-[(3,4-dimethoxyphenyl)methylene]-2,3-dihydro-2-oxo-1H-indole-1-acetic acid, ethyl ester;

3-[[3-(Bicyclo[2.2.1]hept-2-yloxy)-4-methoxyphenyl]methylene]-2,3-dihydro-N,N-dimethyl-2-oxo-[1α,2α(Z),4α]-1H-indole-5-sulfonamide;

(Z)-7-[[3-(Bicyclo[2.2.1]hept-2-yloxy)-4-methoxyphenyl]methylene]-6,7-dihydro-6-oxo-5H-1,3-dioxolo[4,5-f]indole-5-carboxamide;

(E)-7-[[3-(Bicyclo[2.2.1]hept-2-yloxy)-4-methoxyphenyl]methylene]-6,7-dihydro-6-oxo-5H-1,3-dioxolo[4,5-f]indole-5-carboxamide;

3-[[3-(Bicyclo[2.2.1]hept-2-yloxy)-4-methoxyphenyl]methylene]-5-methyl-1,3-dihydro-[1α,2α(E),4α]-2H-indol-2-one;

3-[[3-(Bicyclo[2.2.1]hept-2-yloxy)-4-methoxyphenyl]methylene]-1,5-dimethyl-1,3-dihydro-[1α,2α(E),4α]-2H-indol-2-one;

3-[[3-(Bicyclo[2.2.1]hept-2-yloxy)-4-methoxyphenyl]methylene]-5-methyl-1,3-dihydro-[1α,2α(Z),4α]-2H-indol-2-one;

3-[[3-(Bicyclo[2.2.1]hept-2-yloxy)-4-methoxyphenyl]methylene]-5-chloro-1,3-dihydro-1-methyl-[1α,2α(Z),4α]-2H-pyrrolo[3,2-b]pyridin-2-one;

3-[[3-(Bicyclo[2.2.1]hept-2-yloxy)-4-methoxyphenyl]methylene]-5-chloro-1,3-dihydro-[1α,2α(Z),4α]-2H-indol-2-one;

3-[[3-(Bicyclo[2.2.1]hept-2-yloxy)-4-methoxyphenyl]methylene]-5-chloro-1,3-dihydro-[1α,2α(E),4α]-2H-indol-2-one; and 3-[1-[3-(Bicyclo[2.2.1]hept-2-yloxy)-4-methoxyphenyl]ethylidene]-1,3-dihydro-[1α,2α(E),4α]-2H-indol-2-one.

The present invention also relates to a pharmaceutical composition for treating a condition selected from the group consisting of acquired immunodeficiency syndrome ("AIDS"), asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising an amount of a compound of the formula I, or a pharmaceutically acceptable salt thereof, effective in treating such condition, and a pharmaceutically acceptable carrier.

The present invention also relates to a method of treating a condition selected from the group consisting of AIDS, asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising administering to said mammal an amount of a compound of the formula I, or a pharmaceutically acceptable salt thereof, effective in treating such condition.

The present invention also relates to a pharmaceutical composition for inhibiting the effects of phosphodiesterase type IV in a mammal, including a human, comprising a phosphodiesterase type IV inhibiting amount of a compound of the formula I, or a pharmaceutically acceptable salt thereof, and a pharmaceutically acceptable carrier.

The present invention also relates to a method of inhibiting the effects of phosphodiesterase type IV in a mammal, including a human, comprising administering to said mammal a phosphodiesterase type IV inhibiting amount of a compound of the formula I, or a pharmaceutically acceptable salt thereof.

The present invention also relates to a pharmaceutical composition for treating a condition selected from the group consisting of AIDS, asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising an amount of a compound of the formula I, or a pharmaceutically acceptable salt thereof, effective in inhibiting the action of phosphodiesterase type IV, and a pharmaceutically acceptable carrier.

The present invention also relates to a method of treating a condition selected from the group consisting of AIDS, asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising administering to said mammal an amount of a compound of the formula I, or a pharmaceutically acceptable salt thereof, effective in inhibiting the action of phosphodiesterase type IV.

The present invention also relates to a pharmaceutical composition for treating a disorder in a mammal, including a human, the treatment of which is effected or facilitated by blocking the action of phosphodiesterase type IV, comprising an amount of a compound of the formula I, or a pharmaceutically acceptable salt thereof, effective in treating such disorder, and a pharmaceutically acceptable carrier.

The present invention also relates to a method of treating a disorder in a mammal, including a human, the treatment of which is effected or facilitated by blocking the action of phosphodiesterase type IV, comprising administering to said mammal an amount of a compound of the formula I, or a pharmaceutically acceptable salt thereof, effective in treating such disorder.

Some of the compounds of the present invention have chiral centers and therefore exist in different enantiomeric forms. For example, when the broken line represents a single bond and $R^9$ is not hydrogen, the compound can exist in at least four enantiomeric forms. Some of the compounds of the present invention can also exist in different regioisomeric forms. For example, when the broken line represents a double bond, both the E and Z isomers can be isolated. This invention relates to all optical isomers, all stereoisomers, and all regioisomers of compounds of formula I, and mixtures thereof.

Formula I above includes compounds identical to those depicted but for the fact that one or more hydrogen or carbon atoms are replaced by radioactive isotopes thereof. Such radiolabelled compounds are useful as research and diagnostic tools in metabolism studies, pharmacokinetic studies and in binding assays. Specific applications in research include radioligand binding assays, autoradiography studies and in vivo binding studies, while specific applications in the diagnostic area include studies of selective inhibition of phosphodiesterase type IV in vivo binding in the relevant tissues for asthma, e.g., immune or inflammatory type cells that are directly or indirectly involved in inflammation, and the like.

Also within the scope of this invention are the pharmaceutically acceptable salts of the compounds of the formula I where acidic or basic functionalities are incorporated as substituents. The pharmaceutically acceptable acid salts are those formed from acids which form non-toxic acid salts, for example, hydrochloride, hydrobromide, sulfate, bisulfate, phosphate, acid phosphate, acetate, citrate, fumarate, gluconate, lactate, maleate, succinate, tartrate, methanesulfonate, benzenesulfonate, toluenesulfonate and formate salts. Pharmaceutically acceptable cationic salts include those non-toxic salts based on alkali and alkaline earth metals, for example, sodium, lithium, potassium, calcium and magnesium, as well as non-toxic ammonium, quaternary ammonium and amine cations, for example, ammonium, tetramethylammonium, methylamine, dimethylamine, trimethylamine, ethylamine, diethylamine, triethylamine, N,N'-dibenzylethylenediamine, N-methylglucamine, meglumine, ethanolamine and diethanolamine, The present invention also relates to the following intermediates used in the preparation of compounds of formula I:

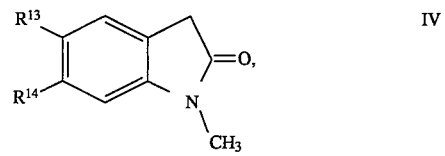

IV wherein $R^{13}$ and $R^{14}$ are independently selected from hydrogen and methoxy;

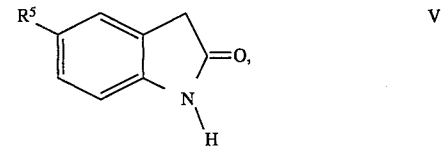

V wherein $R^5$ is $SO_2NR^8R^{12}$;

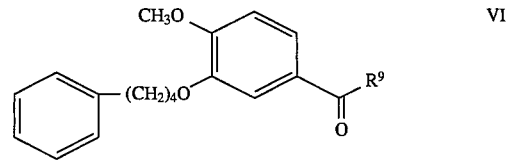

VI wherein $R^9$ is hydrogen or $(C_1-C_6)$alkyl; and

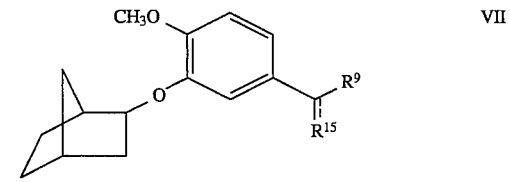

VII wherein $R^9$ is hydrogen or $(C_1-C_6)$alkyl, $R^{15}$ is oxygen or hydroxy, and the broken line represents a double bond when $R^{15}$ is oxygen.

DETAILED DESCRIPTION OF THE INVENTION

The compounds of formula I may be prepared as described in the following reaction schemes and discussion. Unless otherwise indicated, X, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, the broken lines, and the wavy lines in the reaction schemes and discussion that follow are defined as above.

Scheme 1

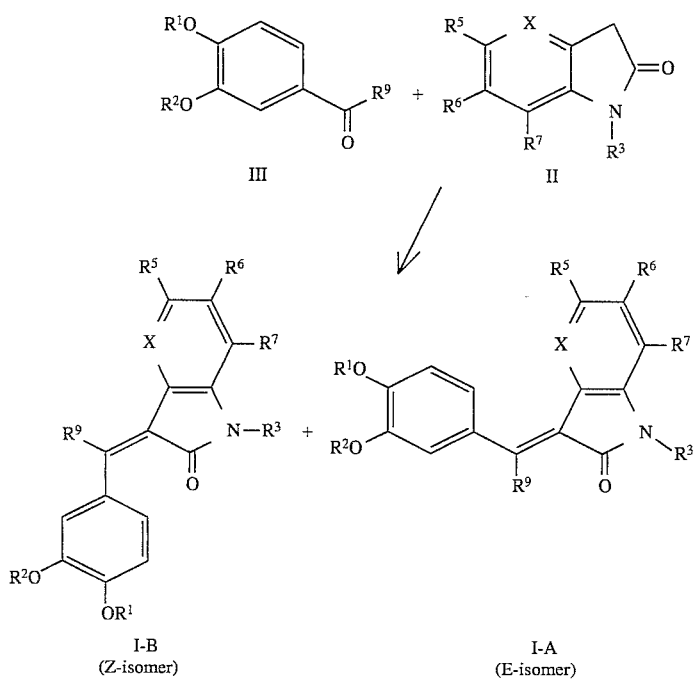

I-B
(Z-isomer)

I-A
(E-isomer)

With reference to reaction Scheme 1, the compounds of the present invention wherein the broken line of formula I represents a double bond (Formulae I-A and I-B), may be prepared by an Aldol condensation, using conditions well known to those skilled in the art. Thus, a compound of formula II is reacted with a compound of formula III, preferably under an inert atmosphere in a reaction inert solvent such as water, methanol, ethanol, butanol, isopropanol, acetone, ether, chloroform, methylene chloride, dioxane, tetrahydrofuran, or dimethoxyethane. To this mixture is added a base such as pyrrolidine, piperidine, diethylamine, triethylamine, Hunig's base, aqueous sodium hydroxide, barium hydroxide, aluminum t-butoxide, sodium ethoxide, potassium hydroxide, morpholine, methyl lithium, butyl lithium, sodium hydride, or pyridine. The actual base utilized will depend somewhat upon the solvent utilized. The reaction mixture is stirred for 2 to 72 hours at a temperature of between 0° and 140°. When the reaction is complete, the compounds of formula I-A (the E isomer) and formula I-B (the Z isomer) are isolated via methods well known to those skilled in the art.

The compounds of formula I-A, wherein $R^3$=hydrogen, can be alkylated to form compounds of formula I-A, wherein $R^3=(C_1-C_6)$alkyl, using reaction conditions well known to one skilled in the art. These reaction conditions can also be performed on compounds of formula I-B, wherein $R^3$=hydrogen, and on compounds of formula II, wherein $R^3$=hydrogen, to effect analogous transformations (and to yield, among other compounds, the compounds of formula IV). Thus, a compound of formula I-A wherein $R^3$ is hydrogen can be combined with a base such as potassium carbonate, sodium hydride, sodium carbonate, sodium hydroxide, potassium hydroxide, potassium t-butoxide, butyl lithium, and potassium fluoride. The mole ratio of starting material oxindole to base will preferably be from about 1.0 to about 0.5. These compounds can be combined in a suitable solvent such as acetone, chloroform, methylene chloride, dimethylformamide, ethanol, butanol, isopropanol, dimethylsulfoxide, or a mixture of two or more of the foregoing solvents. To this mixture, an alkylating agent, such as an alkyl halide or alkyl sulfate, can be added. The reaction can be stirred for a time period from about two to about 72 hours, at a temperature between 0° and 100° C. Additional reagents, such as phase transfer catalysts, can be added. When the reaction is complete, the compounds of formula I-A can be isolated via methods well known to one skilled in the art.

Scheme 2

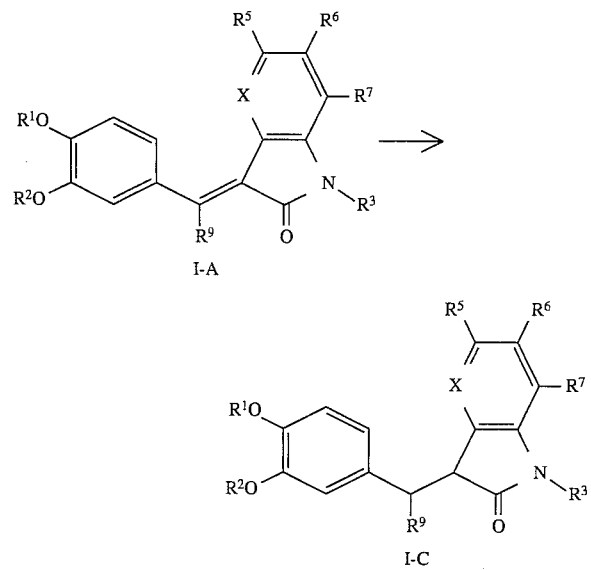

With reference to reaction Scheme 2, the compounds of the present invention wherein the broken line of formula I represents a single bond (formula I-C) can be prepared by a hydrogenation reaction, using reaction conditions well known to one skilled in the art. These reaction conditions can also be performed on compounds of formula I-B to effect analogous transformations. Thus, a compound of formula I-A can be dissolved in a solvent such as ethyl acetate, tetrahydrofuran, methanol, ethanol, butanol, isopropanol, ether, dioxane, chloroform, methylene chloride, dimethoxyethane, or a combination thereof. The mixture can be combined with a catalyst such as palladium, rhodium, Raney nickel, platinum, platinum oxide, palladium hydroxide, nickel boride, ruthenium, zinc oxide, chlorotris(triphenylphosphine)rhodium (Wilkinson's catalyst), or pentacyanocobaltate(II), and shaken under a hydrogen atmosphere for about two to about 72 hours at a pressure of about atmospheric to about 100 atm., at a temperature between 0° and 250°. When the reaction is complete, the compounds of formula I-C can be isolated via methods well known to those skilled in the art. Other possible reducing agents to effect this transformation can be used such as sodium, lithium, chromous ion, zinc sodium hydrophosphate and palladium, trifluoroacetic acid and triethylsilane, hydrazine with an oxidizing agent under reaction conditions well known to one skilled in the art.

The compounds of formula I-A, wherein $R^3$=hydrogen, can also be acylated to form compounds of formula I-A, wherein $R^3$=($C_1$–$C_6$) alkoxycarbonyl, using reaction conditions well known to those skilled in the art. These reaction conditions can also be performed on compounds of formula I-B, wherein $R^3$=hydrogen, and on compounds of formula II, wherein $R^3$=hydrogen, to effect analogous transformations. Thus, a compound of formula I-A wherein $R^3$=hydrogen can be combined with an appropriate acylating agent (such as ethyl chloroformate). In the case of liquid acylating agents, this reagent can also be used as the solvent for the reaction. If, however, the acylating agent is not a liquid, then the solvent for the reaction could be solvents such as dimethylformamide, ethanol, butanol, isopropanol, dimethylsulfoxide, chloroform, or methylene chloride. A base is then added to the reaction mixture; suitable bases include but are not limited to potassium carbonate, sodium hydride, sodium carbonate, sodium hydroxide, potassium hydroxide, potassium t-butoxide, butyl lithium, potassium fluoride, and sodium. Phase transfer catalysts can also be added, if appropriate. The reaction can be stirred at a temperature between 0° and 150° C., for a period of time from about three to about 72 hours. When the reaction is complete, the compounds of formula I-A can be isolated via methods well known to those skilled in the art.

The compounds of formula I-A, wherein $R^4$ $R^5$, $R^6$ and/or $R^7$=hydroxy, can also be acylated to form compounds of formula I-A, wherein $R^4$, $R^5$, $R^6$, and/or $R^7$=($C_2$–$C_6$) acyloxy, using reaction conditions well known to those skilled in the art. These reaction conditions can also be performed on compounds of formula I-B, wherein $R^4$, $R^5$, $R^6$, and/or $R^7$=hydroxy, and on compounds of formula II wherein $R^4$, $R^5$, $R^6$ and/or $R^7$=hydroxy, to effect analogous transformations. Thus, a compound of formula I-A wherein $R^4$, $R^5$, $R^6$, and/or $R^7$=hydroxy, can be combined with a base such as aqueous sodium hydroxide, piperidine, diethylamine, triethylamine, Hunig's base, barium hydroxide, aluminum t-butoxide, sodium ethoxide, potassium hydroxide, morpholine, methyl lithium, butyl lithium, sodium hydride, pyridine, mercury oxide or potassium carbonate in a solvent such as water, methanol, ethanol, butanol, isopropanol, acetone, ether, dioxane, chloroform, methylene chloride, tetrahydrofuran, dimethoxyethane, dimethylsulfoxide, dimethylformamide, or a mixture of two or more of the foregoing solvents, depending on the choice of base. The resulting mixture can be stirred at a temperature between 0° and 150° C. An acylating agent can then be added to this mixture, such as acyl anhydride or acyl halide. The reaction can be stirred for about one-half to about 72 hours. Phase transfer catalysts can be added, if appropriate. When the reaction is complete, the compounds of formula I-A can be isolated via methods well known to those skilled in the art.

The compounds of formula I-A, wherein $R^4$, $R^5$, $R^6$, and/or $R^7$=hydroxy, can also be alkylated to form compounds of formula I-A, wherein $R^4$, $R^5$, $R^6$, and/or $R^7$=($C_1$–$C_8$) alkoxy, ($C_3$–$C_7$) cycloalkoxy, phenyl-($C_1$–$C_6$)alkoxy, or ($C_6$–$C_{12}$) polycycloalkoxy, using reaction conditions well known to those skilled in the art. These reaction conditions can also be performed on compounds of formula I-B, wherein $R^4$, $R^5$, $R^6$, and/or $R^7$=hydroxy, and on compounds of formula II, wherein $R^4$, $R^5$, $R^6$, and/or $R^7$=hydroxy, as well as on compounds of formula III wherein $R^1$ and/or $R^2$=hydroxy, to effect analogous transformations (and to yield, among other compounds, the compounds of formula VI). Thus, a compound of formula I-A wherein $R^4$, $R^5$, $R^6$, and/or $R^7$=hydroxy, can be dissolved in a reaction inert solvent such as acetone, ether, chloroform, methylene chloride, dioxane, tetrahydrofuran, dimethoxyethane, dimethylsulfoxide, dimethylformamide, or a mixture of two or more of the foregoing solvents. To this mixture is added a base such as aqueous sodium hydroxide, barium hydroxide, aluminum t-butoxide, sodium methoxide, sodium ethoxide, potassium hydroxide, potassium carbonate, methyl lithium, butyl lithium, sodium hydride, silver oxide, potassium fluoride, or tetraethylammonium fluoride. The choice of base may depend somewhat on the choice of solvent. The reaction mixture can be stirred for about one-half hour to about 3 hours, at a temperature between –78° C. and room temperature. Upon formation of the alkoxide, the alkylating agent such as an alkyl halide, or alkyl sulfate is added. Additional reagents can be added, such as hexamethylphosphoramide, potassium iodide, sodium iodide, or phase transfer catalysts. The reaction mixture is then stirred for one to 24 hours, at a temperature between –20° C. and 150° C. When the reaction is complete, the compounds of the formula I-A can be isolated via methods well known to those skilled in the art.

Alternatively, this transformation could be carried out under the following reaction conditions. A compound of formula I-A wherein $R^4$, $R^5$, $R^6$, and/or $R^7$=hydroxy, can be dissolved in a reaction inert solvent such as ether, chloroform, methylene chloride, dioxane, tetrahydrofuran, dimethoxyethane, dimethylsulfoxide, dimethylformamide, or a mixture of two or more of the foregoing solvents. The alkylation is then performed using an alkylating agent such as an alkyl alcohol, in combination with a triarylphosphine or trialkyl phosphine, and a dialkylazodicarboxylate. The reaction mixture can be stirred for about 2 to about 150 hours, at a temperature between 0° and 150° C. When the reaction is complete, the compounds of formula I-A can be isolated via methods well known to those skilled in the art.

The compounds of formula I-A, wherein $R^3$=hydrogen, can also be alkylated to form compounds of formula I-A wherein $R^3$=($C_1$–$C_6$) alkoxycarbonyl-($C_1$–$C_6$)alkyl, using reaction conditions well known to one skilled in the art. These reaction conditions can also be performed on compounds of formula I-B, wherein $R^3$=hydrogen, and on compounds of formula II, wherein $R^3$=hydrogen, to effect analogous transformations. Thus, a compound of formula I-A wherein $R^3$ is hydrogen can be dissolved with an alkoxycarbonyl alkylating agent such as ethyl chloroacetate in a solvent such as dimethylformamide, acetone, ether, chloroform, methylene chloride, dioxane, tetrahydrofuran, dimethoxy ethane, dimethylsulfoxide, or a mixture of two or more of the foregoing solvents. The reaction can be cooled, and then a base can be added such as sodium hydride, aqueous sodium hydroxide, barium hydroxide, aluminum t-butoxide, sodium methoxide, sodium ethoxide, potassium hydroxide, potassium carbonate, methyl lithium, butyl lithium, silver oxide, potassium fluoride, or tetraethylammonium fluoride. The reaction can then be stirred for about 10 minutes to 72 hours, at a temperature between $-20°$ and 150° C. Additional reagents can be added such as hexamethylphosphoramide, potassium iodide, or sodium iodide. When the reaction is complete, the compounds of formula I-A can be isolated via methods well known to those skilled in the art.

The compounds of formula I-A, wherein $R^4$, $R^5$, $R^6$, and/or $R^7$=nitro, can also be reduced to form compounds of formula I-A, wherein $R^4$, $R^5$, $R^6$, and/or $R^7$=amino, using reaction conditions well known to those skilled in the art. These reactions can also be performed on compounds of formula I-B, wherein $R^4$, $R^5$, $R^6$, and/or $R^7$=nitro, and on compounds of formula II, wherein $R^4$, $R^5$, $R^6$, and/or $R^7$=nitro, to effect analogous transformations. Thus, a compound of formula I-A wherein $R^4$, $R^5$, $R^6$, and/or $R^7$=nitro, can be combined with a reducing agent in a solvent such as water, methanol, ethanol, butanol, isopropanol, acetone, ether, dioxane, chloroform, methylene chloride, tetrahydrofuran, dimethoxyethane, dimethylsulfoxide, dimethylformamide, or a mixture of two or more of the foregoing solvents. Examples of reducing agents are iron powder, zinc, tin, hydrogen chloride, acetic acid, formic acid, sulfuric acid, catalytic hydrogenation, titanium trichloride, sodium sulfide, ammonium sulfide, polysulfides, sodium dihydro(t-rithio)borate, sodium borohydride with nickel chloride or cobalt chloride, or hydrazine with a catalyst (e.g. palladium on carbon). The mixture can be stirred at a temperature between 0° and 200° C., for a time period of from about one half to about 72 hours. When the reaction is complete, the compounds of formula I-A can be isolated via methods well known to those skilled in the art.

Reaction schemes 3 and 4 illustrate the preparation of intermediates of the present invention.

Scheme 3

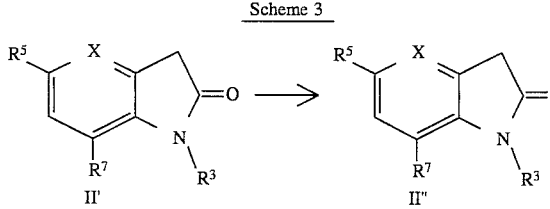

With reference to reaction Scheme 3, the compounds of formula II', wherein $R^4$, $R^5$, $R^6$, and/or $R^7$=hydrogen, can also be alkylated, acylated, or sulfonylated to form compounds of formula II", wherein $R^4$, $R^5$, $R^6$, and/or $R^7$=$(C_1-C_6)$alkyl, $(C_1-C_6)$ alkylcarbonyl, or $SO_2NR^8R^{12}$ (of which the compounds of formula V are an example), using reaction conditions well known to those skilled in the art. Thus, to a suspension of a Lewis acid such as aluminum chloride, boron trifluoride, zinc chloride, gallium chloride, ferric chloride, or tin chloride, in a solvent such as carbon disulfide, acetone, ether, chloroform, methylene chloride, dioxane, tetrahydrofuran, dimethoxyethane, nitrobenzene, acetic acid, or a mixture of two or more of the foregoing solvents, was added an alkyl halide, such as ethyl chloride, an acyl halide, such as acetyl chloride, or a substituted sulfuryl halide, such as dimethylsulfamoyl chloride. This is followed by addition of a compound of formula II' wherein $R^4$, $R^5$, $R^6$, and/or $R^7$=hydrogen. The reaction can be stirred at a temperature between 0° and 250° C., for a period of time from about 2 to about 72 hours. When the reaction is complete, the compounds of formula II" can be isolated via methods well known to those skilled in the art. The compounds of formula II' are generally commercially available or are known to those skilled in the art.

Scheme 4

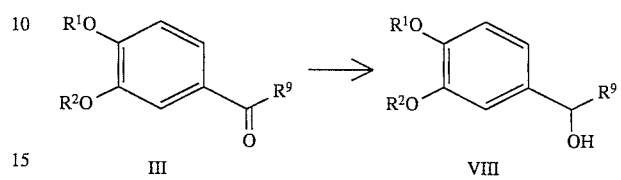

With reference to reaction Scheme 4, the compounds of formula III, wherein $R^9$=hydrogen, can be reacted to form compounds of formula VIII, wherein $R^9$=$(C_1-C_6)$ alkyl (of which the compounds of formula VII are an example), using reaction conditions well known to those skilled in the art. Thus, a compound of formula III wherein $R^9$ is H can be dissolved in a solvent such as ether, dioxane, tetrahydrofuran, dimethoxyethane, hexane, pentane, or a mixture of two or more of the foregoing solvents. The reaction mixture can be cooled to a temperature between $-100°$ and 20° C., and then a suitable organometallic reagent can be added such as organomagnesium halide, organolithium, organocuprate, organozinc, organotitanium, organozirconium, or organomanganese. Other additives can also be utilized, such as hexamethylphosphoramide, N,N,N',N'-tetramethylenediamine, amino alcohol, titanium halide, zirconium halide, dibromoethane, iodine, or combinations thereof. The reaction can be stirred for a period of time of from about one half to about 150 hours, at a temperature between 0° C. and 150° C. When the reaction is complete, compounds of formula VIII can be isolated via methods well known to those skilled in the art. The compounds of formula III are generally commercially available or known to those skilled in the art.

The compounds of formula VIII, wherein $R^9$=$(C_1-C_6)$alkyl, can be oxidized to form compounds of formula III, wherein $R^9$=$(C_1-C_6)$alkyl, using reaction conditions well known to those skilled in the art. Thus, a compound of formula VIII can be combined with a solvent such as water, acetone, acetic acid, trifluoroacetic acid, dimethylformamide, dimethylsulfoxide, ether, dioxane, tetrahydrofuran, dimethoxyethane, hexane, pentane, pyridine, chloroform, methylene chloride, benzene, or a mixture of two or more of the foregoing solvents, and the mixture can be cooled to a temperature between $-20°$ and 15° C. An oxidizing reagent can then be added, such as acid dichromate, potassium permanganate, bromine, manganese dioxide, ruthenium tetroxide, Jones reagent (chromic acid and sulfuric acid in water), Collin's reagent (dipyridine chromium (VI) oxide), pyridinium chlorochromate, pyridinium dichromate, sodium hypochlorite, dimethyl sulfoxide, tetrapropylammonium perruthenate, ceric ammonium nitrate, silver carbonate, hydrogen peroxide, Fremy's salt, m-chloroperbenzoic acid, aluminum t-butoxide, N-halosuccinimide, dicyclohexylcarbodiimide, or chromium trioxide. The mixture can then be allowed to warm to about room temperature and then stirred for about one half to about 150 hours. Additional additives can be utilized, such as hexamethylphosphoramide, phase transfer catalysts, or tetrabutylammonium iodide. When the reaction is complete, the compounds of the formula III can be isolated via methods well known to those skilled in the art.

The preparation of other compounds of the present invention not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and their pharmaceutically acceptable salts (hereinafter referred to, collectively, as "the active compounds of the present invention") are useful as selective inhibitors of phosphodiesterase type IV, i.e., they possess the ability to inhibit the effects of phosphodiesterase type IV in mammals, and therefore they are able to function as therapeutic agents in the treatment of the aforementioned disorders and diseases in an afflicted mammal.

Those compounds of the present invention which are basic in nature (such as those compounds of formula I, wherein $R^4$, $R^5$, $R^6$, and/or $R^7=NR^8R^{12}$) are capable of forming a wide variety of different salts with various inorganic and organic acids. Although such salts must be pharmaceutically acceptable for administration to animals, it is often desirable in practice to initially isolate a compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. Pharmaceutically-acceptable acid addition salts of the compounds of this invention include, but are not limited to, those formed with hydrochloric acid (HCl), hydrobromic acid (HBr), nitric acid ($HNO_3$), sulfuric acid ($H_2SO_4$), phosphoric acid ($H_3PO_4$), methanesulfonic acid ($CH_3SO_3H$), toluenesulfonic acid (p-$CH_3C_6H_4SO_3H$), acetic acid ($CH_3CO_2H$), gluconic acid, tartaric acid, maleic acid and succinic acid. Those compounds of the present invention which are acidic in nature are capable of forming a wide variety of different salts with various inorganic and organic bases. Pharmaceutically-acceptable cationic salts of the compounds of this invention include, but are not limited to, those of sodium, potassium, calcium, magnesium, ammonium, N,N'-dibenzylethylenediamine, N-methylglucamine (meglumine), ethanolamine and diethanolamine.

The compounds of the present invention and their pharmaceutically acceptable salts exhibit phosphodiesterase type IV receptor-binding activity and therefore are of value in the treatment of a wide variety of clinical conditions the treatment of which are effected or facilitated by a decrease in phosphodiesterase type IV mediated activity. Such conditions include AIDS, asthma, rheumatoid arthritis, osteoarthritis, bronchitis, chronic obstructive airways disease, psoriasis, allergic rhinitis, atopic dermatitis, shock, and other inflammatory diseases. Hence, these compounds are readily adapted to therapeutic use as selective inhibitors of phosphodiesterase type IV for the control and/or treatment of any of the aforesaid clinical conditions in mammals, including humans.

The compounds of the present invention are readily adapted to clinical use as selective inhibitors of phosphodiesterase type IV. The ability of the compounds or the pharmaceutically acceptable salts thereof to inhibit phosphodiesterase type IV may be shown by the following Human Lung in vitro assay.

Thirty to forty grams of human lung tissue is placed in 50 ml of pH 7.4 Tris/phenylmethylsulfonyl fluoride (PMSF)/sucrose buffer and homogenized using a Tekmar Tissumizer® (Tekmar Co., 7143 Kemper Road, Cincinnati, Ohio 45249) at full speed for 30 seconds. The homogenate is centrifuged at 48,000×g for 70 minutes at 4° C. The supernatant is filtered twice through a 0.22 μm filter and applied to a Mono-Q FPLC column (Pharmacia LKB Biotechnology, 800 Centennial Avenue, Piscataway, N.J. 08854) pre-equilibrated with pH 7.4 Tris/PMSF buffer. A flow rate of 1 ml/minute is used to apply the sample to the column, followed by a 2 ml/minute flow rate for subsequent washing and elution. Sample is eluted using an increasing, step-wise sodium chloride gradient in the pH 7.4 Tris/PMSF buffer. Eight ml fractions are collected. Fractions are assayed for specific PDE IV activity, determined by [$^3$H]cAMP hydrolysis and the ability of a known PDE IV inhibitor (e.g. rolipram) to inhibit that hydrolysis. Appropriate fractions are pooled, diluted with ethylene glycol (2 ml ethylene glycol/5 ml of enzyme prep) and stored at −20° C. until use.

Compounds are dissolved in dimethylsulfoxide (DMSO) at a concentration of 10 mM and diluted 1:25 in water (400 μM compound, 4% DMSO). Further serial dilutions are made in 4% DMSO to achieve desired concentrations. Final DMSO concentration in assay tube is 1%. In duplicate the following are added, in order, to a 12×75 mm glass tube (all concentrations are given as final concentrations in assay tube).

i) 25 μl compound or DMSO (1%, for control and blank)
ii) 25 μl pH 7.5 Tris buffer
iii) [$^3$H]cAMP (1 μM)
iv) 25 μl PDE IV enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazineethanesulfonic acid (HEPES)/0.1M NaCl, pH 8.5) is added to each tube on an ice bath. The contents of each tube are applied to an Affi-Gel 601 column (Biorad Laboratories, P.O. Box 1229, 85A Marcus Drive, Melville, N.Y. 11747) (boronate affinity gel, 1 ml bed volume) previously equilibrated with washing buffer. [$^3$H]cAMP is washed with 2×6 ml washing buffer, and [$^3$H]5'AMP is then eluted with 4 ml of 0.25M acetic acid. After vortexing, 1 ml of the elution is added to 3 ml scintillation fluid in a suitable vial, vortexed and counted for [$^3$H].

$$\% \text{ Inhibition} = 1 - \frac{\text{average cpm (test compound)} - \text{average cpm (blank)}}{\text{average cpm (control)} - \text{average cpm (blank)}}$$

$IC_{50}$ is defined as that concentration of compound which inhibits 50% of specific hydrolysis of [$^3$H]cAMP to [$^3$H]5'AMP.

For treatment of the various conditions described above, the compounds of the invention and their pharmaceutically acceptable salts can be administered to the patient either alone or, preferably, in combination with pharmaceutically acceptable carriers or diluents in a pharmaceutical composition according to standard pharmaceutical practice. Such administration may be carried out in single or multiple doses. A compound can be administered via a variety of conventional routes of administration including orally, parenterally, by inhalation, and topically. When the compounds are administered orally, the dose range will generally be from about 0.1 to about 500 mg/day for an average adult patient (70 kg), preferably from about 7 to about 70 mg/day in single or divided doses. If parenteral administration is desired, then an effective dose will generally be from about 0.1 to about 70 mg/day. For intranasal or inhaler administration, the dosage will generally be formulated as a 0.1 to 1% (w/v) solution. In some instances it may be necessary to use dosages outside these limits, since the dosage will necessarily vary according to the species, age, weight, and response of the individual patient, severity of the patient's symptoms, potency of the particular compound being administered, type of pharmaceutical formulation chosen, and time period and interval at which administration is carried out.

The compounds of the invention and their pharmaceutically acceptable salts can be administered in a wide variety of different dosage forms, such as in the form of tablets, powders, lozenges, troches, hard candies, sprays, creams, salves, suppositories, jellies, gels, pastes, lotions, ointments, syrups or capsules, aqueous solutions or suspensions, injectable solutions, elixirs, and the like. Such carriers include solid diluents or fillers, sterile aqueous media and various non-toxic organic solvents, etc. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered (preferably pH greater than 8) if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically and this may preferably be done by way of creams, jellies, gels, pastes, ointments and the like, in accordance with standard pharmaceutical practice.

The present invention is illustrated by the following Examples and Preparations. It will be understood, however, that the invention is not limited to the specific details of these Examples and Preparations. All melting points are uncorrected. In the procedures and tables that follow, "stchm" means stereochemistry, "Ex." means Example, "mp(°C.)" means melting point in degrees Celcius, "MF" means molecular formula, "Anal." means elemental analysis, "Calc" means calculated, "m/z" means mass to charge ratio, "H" means hydrogen, "C" means carbon, "O" means oxygen, "Me" means methyl, "Et" means ethyl, "Br" means bromine, and "Cl" means chlorine.

EXAMPLES

EXAMPLES 1 AND 2

3-[[3-(Bicyclo[2.2.1]hept-2-yloxy)-4-methoxyphenyl]methylene]-5-chloro-1,3-dihydro-1-methyl-[1α,2α(Z),4α]-2H-indol-2-one (Example 1) and 3-[[(Bicyclo[ 2.2.1]-hept-2-yloxy)-4-methoxyphenyl]methylene]-5-chloro-1,3-dihydro-1-methyl-[1α,2α(E),4α]-2H-indol-2-one (Example 2)

3-(exo-Bicyclo[2.2.1]hept-2-yloxy)-4-methoxybenzaldehyde (677 mg, 2.75 mmol; disclosed in WO 87/06576 published Nov. 5, 1987), and 5-chloro-1-methyloxindole (500 mg, 2.75 mmol; Chemical Abstracts registry number 41192-33-0, were dissolved in 10 ml of methanol under an inert atmosphere. To this brown, homogeneous mixture was added 0.23 ml of pyrrolidine (2.75 mmol) via syringe. The reaction mixture was stirred at room temperature for ten hours. The solvent was then stripped off and the resulting yellow oil was purified via flash chromatography (1:1 ethyl ether/hexane) to provide the desired Z-adduct 3-[[3-(bicyclo [2.2.1]hept-2-yloxy)-4-methoxyphenyl]methylene]-5-chloro-1,3-dihydro-1-methyl-[1α,2α(Z),4α]-2H-indol-2-one (125 mg, 11% yield) as a yellow solid (Example 1): m.p. 149°–151°. Analysis calculated for $C_{24}H_{24}ClNO_3$: C, 70.32; H, 5.90; N, 3.42. Found: C, 70.26; H, 5.87; N, 3.38. The corresponding E-adduct 3-[[3-(bicyclo[2.2.1]hept-2-yloxy)-4-methoxyphenyl]methylene]-5-chloro-1,3-dihydro-1-methyl-[1α,2α(E),4α]-2H-indol-2-one (Example 2) was also obtained in 6% yield, m.p. 142°–144° C. Analysis calculated for $C_{24}H_{24}ClNO_3$: C, 70.32; H, 5.90; N, 3.42. Found: C, 70.34; H, 5.85; N, 3.36.

EXAMPLES 3–41

Following the method of Example 1, the following products were prepared by reacting 3-(exo-bicyclo[2.2.1]hept-2 -xyloxy)-4-methoxy benzaldehyde with an appropriate oxindole (as determined by $R^5$ and $R^6$ indicated below) in place of the 5-chloro-1 -methyloxindole. Unless otherwise indicated, the starting material oxindole is either known in the literature or is commercially available. The wavy lines indicate that the following compounds can exist as either the E or Z stereoisomers:

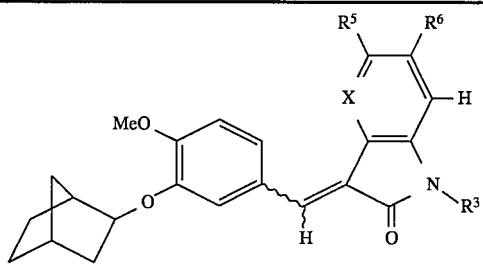

| Ex. | $R^3$ | $R^5$ | $R^6$ | X | Stchm | mp (°C.) | MF for Analysis | Anal. | C | H | N | MF for m/z | m/z |
|---|---|---|---|---|---|---|---|---|---|---|---|---|---|
| 3 | H | H | H | C—H | E | 204–205 | $C_{23}H_{23}NO_3$ | Calc: Found | 76.43 76.24 | 6.41 6.35 | 3.88 3.88 | | |
| 4 | H | H | H | C—H | Z | 186–187 | $C_{23}H_{23}NO_3 \cdot \frac{1}{4}H_2O$ | Calc: Found | 75.49 75.84 | 6.47 6.17 | 3.83 3.81 | $C_{23}H_{23}NO_3$ | Calc: 361.1678 Found: 361.17835 |
| 5 | Me | H | H | C—H | E | 80–110 | $C_{24}H_{25}NO_3 \cdot \frac{1}{2}H_2O$ | Calc: Found | 74.98 75.35 | 6.82 6.46 | 3.64 3.66 | $C_{24}H_{25}NO_3$ | Calc: 375.1834 Found: 375.1830 |
| 6 | Me | H | H | C—H | Z | 116–117 | $C_{24}H_{25}NO_3$ | Calc: Found | 76.78 76.68 | 6.71 6.55 | 3.73 3.71 | | |
| 7 | Et | H | H | C—H | E | 143–144 | $C_{25}H_{27}NO_3$ | Calc: Found | 77.09 77.05 | 6.99 7.07 | 3.60 3.59 | | |
| 8 | Et | H | H | C—H | Z | foam | $C_{25}H_{27}NO_3 \cdot \frac{1}{2}H_2O$ | Calc: Found | 75.35 75.75 | 7.08 7.12 | 3.51 3.78 | $C_{25}H_{27}NO_3$ | Calc: 389.1991 Found: 389.1970 |
| 9 | H | OH | H | C—H | E | 145–157 | $C_{23}H_{23}NO_4 \cdot \frac{3}{4}H_2O$ | Calc: Found | 70.66 70.55 | 6.32 6.10 | 3.58 3.53 | $C_{23}H_{23}NO_4$ | Calc: 377.1627 Found: 377.1606 |
| 10 | H | OH | H | C—H | Z | 162–164 | $C_{23}H_{23}NO_4 \cdot \frac{1}{2}H_2O$ | Calc: Found | 71.49 71.88 | 6.26 5.92 | 3.62 3.76 | $C_{23}H_{23}NO_4$ | Calc: 377.1627 Found: 377.1620 |
| 11 | Et | OH | H | C—H | Z | 212–213 | $C_{25}H_{27}NO_4 \cdot \frac{1}{4}H_2O$ | Calc: Found | 73.24 72.97 | 6.76 6.76 | 3.42 3.42 | $C_{25}H_{27}NO_4$ | Calc: 405.1940 Found: 405.18512 |
| 12 | H | H | OMe | C—H | Z | 187–189 | $C_{24}H_{25}NO_4 \cdot \frac{1}{4}H_2O$ | Calc: Found | 72.80 72.72 | 6.49 6.34 | 3.54 3.55 | $C_{24}H_{25}NO_4$ | Calc: 391.1784 Found: 391.17407 |
| 13 | $CONH_2$ | $OCH_2O$ ($R^5$ and $R^6$ connected) | see $R^5$ | C—H | E | 191–193 | | | | | | $C_{25}H_{24}N_2O_6$ | Calc: 448.1634 Found: 448.16474 |
| 14 | $CONH_2$ | $OCH_2O$ ($R^5$ and $R^6$ connected) | see $R^5$ | C—H | Z | 189–191 | $C_{25}H_{24}N_2O_6$ | Calc: Found | 66.95 67.07 | 5.39 5.01 | 6.25 6.30 | $C_{25}H_{24}N_2O_6$ | Calc: 448.1634 Found: 448.16789 |
| 15 | H | Br | H | C—H | E | 212–213 | $C_{23}H_{22}BrNO_3$ | Calc: Found | 62.74 62.47 | 5.04 4.88 | 3.18 3.27 | | |
| 16 | H | Br | H | C—H | Z | 178–179 | $C_{23}H_{22}BrNO_3$ | Calc: Found | 62.74 62.48 | 5.04 4.90 | 3.18 3.08 | | |
| 17 | H | Cl | H | C—H | E | 229–230 | $C_{23}H_{22}ClNO_3$ | Calc: Found | 69.78 69.80 | 5.60 5.48 | 3.54 3.48 | | |
| 18 | H | Cl | H | C—H | Z | 191–192 | $C_{23}H_{22}ClNO_3$ | Calc: Found | 69.78 69.45 | 5.60 5.55 | 3.54 3.53 | | |
| 19 | $CONH_2$ | Cl | H | C—H | E | 209–211 | $C_{24}H_{23}ClN_2O_4$ | Calc: Found | 65.68 65.37 | 5.28 5.27 | 6.38 6.25 | | |
| 20 | $CONH_2$ | Cl | H | C—H | Z | 198–200 | $C_{24}H_{23}ClN_2O_4$ | Calc: Found | 65.68 65.97 | 5.28 5.12 | 6.38 6.16 | | |
| 21 | H | H | Cl | C—H | E | 243–245 | $C_{23}H_{22}ClNO_3$ | Calc: Found | 69.78 69.49 | 5.60 5.47 | 3.54 3.50 | | |
| 22 | H | H | Cl | C—H | Z | 184–186 | $C_{23}H_{22}ClNO_3 \cdot \frac{1}{4}H_2O$ | Calc. Found | 68.99 68.86 | 5.66 5.51 | 3.50 3.52 | $C_{23}H_{22}ClNO_3$ | Calc: 395.1288 Found: 395.1287 |
| 23 | OMe | H | Cl | C—H | E | 123–126 | $C_{24}H_{24}ClNO_4$ | Calc: Found | 67.68 67.33 | 5.68 5.58 | 3.29 3.35 | | |
| 24 | OMe | H | Cl | C—H | Z | 131–133 | | | | | | $C_{24}H_{24}ClNO_4$ | Calc: 425.1394 |

-continued

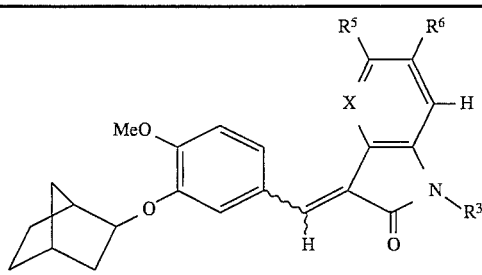

| Ex. | R³ | R⁵ | R⁶ | X | Stchm | mp (°C.) | MF for Analysis | Anal. | C | H | N | MF for m/z | m/z |
|---|---|---|---|---|---|---|---|---|---|---|---|---|---|
| 25 | H | NO₂ | H | C—H | E | 270–272 | $C_{23}H_{22}N_2O_5 \cdot \frac{1}{2}H_2O$ | Calc: Found: | 66.50 66.38 | 5.58 5.24 | 6.74 6.84 | $C_{23}H_{22}N_2O_5$ | Found: 425.1396 Calc: 406.1529 Found: 406.1505 |
| 26 | H | NO₂ | H | C—H | Z | 203–206 | $C_{23}H_{22}N_2O_5$ | Calc: Found: | 67.97 67.73 | 5.46 5.16 | 6.89 6.82 | | |
| 27 | H | NO₂ | H | C—H | E | 317–321 | $C_{23}H_{21}N_3O_7 \cdot \frac{1}{4}H_2O$ | Calc: Found: | 60.59 60.55 | 4.75 4.57 | 9.22 8.98 | $C_{23}H_{21}N_3O_7$ | Calc: 451.1380 Found: 451.1387 |
| 28 | H | Cl | H | N | E | 246–247 | $C_{22}H_{21}ClN_2O_3$ | Calc: Found: | 66.58 66.28 | 5.33 5.08 | 7.06 7.43 | | |
| 29 | H | H | H | N | E | 197–198 | $C_{22}H_{22}N_2O_3 \cdot \frac{1}{8}H_2O$ | Calc: Found: | 72.46 72.40 | 6.15 6.04 | 7.68 7.62 | $C_{22}H_{22}N_2O_3$ | Calc: 362.1630 Found: 362.16102 |
| 30 | H | Me | H | C—H | E | 199–200 | | | | | | $C_{24}H_{25}NO_3$ | Calc: 375.1834 Found: 375.1863 |
| 31 | H | Me | H | C—H | Z | 135–141 | $C_{24}H_{25}NO_3$ | Calc: Found: | 76.78 76.47 | 6.71 6.72 | 3.73 3.56 | | |
| 32 | H | COMe | H | C—H | E | 200–202 | $C_{25}H_{25}NO_4 \cdot \frac{1}{2}H_2O$ | Calc: Found: | 72.80 73.03 | 6.35 6.33 | 3.40 3.33 | $C_{25}H_{25}NO_4$ | Calc: 403.1784 Found: 403.1778 |
| 33 | H | COMe | H | C—H | Z | 128–132 | $C_{25}H_{25}NO_4 \cdot \frac{1}{2}H_2O$ | Calc: Found: | 72.80 73.15 | 6.35 6.42 | 3.40 3.50 | $C_{25}H_{25}NO_4$ | Calc: 403.1784 Found: 403.1814 |
| 34 | Me | OMe | H | C—H | E | 119–121 | $C_{25}H_{27}NO_4 \cdot \frac{1}{8}H_2O$ | Calc: Found: | 73.64 73.31 | 6.74 6.36 | 3.44 3.24 | $C_{25}H_{27}NO_4$ | Calc: 405.1940 Found: 405.1920 |
| 35 | Me | OMe | H | C—H | Z | foam | $C_{25}H_{27}NO_4$ | Calc: Found: | 74.05 73.80 | 6.71 6.88 | 3.45 3.15 | | |
| 36 | Me | H | OMe | C—H | E | 154–156 | | | | | | $C_{25}H_{27}NO_4$ | Calc: 405.1940 Found: 405.19276 |
| 37 | Me | H | OMe | C—H | Z | 111.5–113 | $C_{25}H_{27}NO_4$ | Calc: Found: | 74.05 74.10 | 6.71 6.69 | 3.45 3.47 | | |
| 38 | Me | OMe | OMe | C—H | E | 186–187 | $C_{26}H_{29}NO_5 \cdot \frac{1}{4}H_2O$ | Calc: Found: | 70.97 70.82 | 6.76 6.58 | 3.18 3.11 | $C_{26}H_{29}NO_5$ | Calc: 435.2046 Found: 435.20705 |
| 39 | Me | OMe | OMe | C—H | Z | 123–125 | $C_{26}H_{29}NO_5$ | Calc: Found: | 71.71 71.49 | 6.71 6.65 | 3.22 3.29 | | |
| 40 | H | SO₂NMe₂ | H | C—H | E | 253–254 | $C_{25}H_{28}N_2O_5S$ | Calc: Found: | 64.08 63.92 | 6.02 5.78 | 5.98 5.78 | | |
| 41 | H | SO₂NMe₂ | H | C—H | Z | 180–200 | $C_{25}H_{28}N_2O_5S \cdot \frac{1}{2}H_2O$ | Calc: Found: | 62.88 62.88 | 6.12 6.07 | 5.87 5.82 | $C_{25}H_{28}N_2O_5S$ | Calc: 468.1719 Found: 468.1698 |

R⁷ in Example 27 is NO₂. The starting material oxindole for Examples 34 and 35 is prepared in Preparation A, infra. The starting material oxindole for Examples 36 and 37 is prepared in PREPARATION B, infra. The starting material oxindole for Examples 38 and 39 is prepared in PREPARATION C, infra. The starting material oxindole for Examples 40 and 41 is prepared in PREPARATION D, infra.

EXAMPLES 42–45

Following the method of Example 1, the following products were prepared by reacting an appropriate substituted benzaldehyde, in place of 3-(exo-bicyclo[2.2.1]hept-2-yloxy)-4-methoxy benzaldehyde of Example 1, with oxindole. Unless otherwise indicated, the starting material benzaldehyde is either known in the literature or is commercially available. The wavy lines indicate that these compounds can exist as either the E or Z stereoisomers as indicated below.

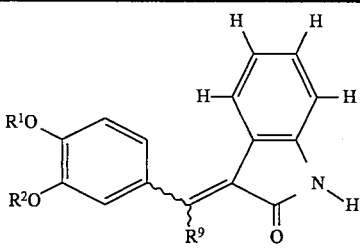

| Ex. | $R^1$ | $R^2$ | $R^9$ | Stchm | mp (°C.) | MF for Analysis | Anal. | C | H | N | MF for m/z | m/z |
|---|---|---|---|---|---|---|---|---|---|---|---|---|
| 42 | see $R^2$ | $CH_2CH_2$ ($R^1$ and $R^2$ connected) | H | E | 203–205 | | | | | | $C_{17}H_{13}NO_3$ | Calc: 279.0895 Found: 279.0885 |
| 43 | see $R^2$ | $CH_2CH_2$ ($R^1$ and $R^2$) connected | H | Z | 210–211 | $C_{17}H_{13}NO_3$ | Calc: Found: | 73.11 72.86 | 4.69 4.53 | 5.02 4.95 | | |
| 44 | Me | $(CH_2)_4C_6H_5$ | H | E | 185–186 | $C_{26}H_{25}NO_3$ | Calc: Found: | 78.17 78.05 | 6.31 6.22 | 3.51 3.48 | | |
| 45 | Me | 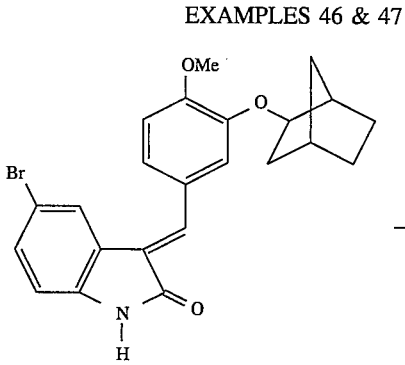 | Me | Z | 219–221 | $C_{24}H_{25}NO_3 \cdot H_2O$ | Calc: Found: | 73.26 73.34 | 6.92 6.49 | 3.55 3.51 | $C_{24}H_{25}NO_3$ | Calc: 375.1834 Found: 375.18346 |

The starting material benzaldehyde for Example 44 is prepared in PREPARATION E, infra. The starting material benzaldehyde for Example 45 is prepared in PREPARATIONS F & G, infra.

EXAMPLES 46 & 47

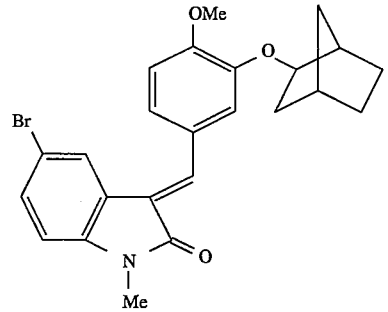

3-[[3-(Bicyclo[2.2.1]hept-2-yloxy)-4-methoxphenyl]methylene]-5-bromo-1,3-dihydro-1-methyl-[1α,2α(E),4α]-2H-indol-2-one (Example 46) and 3-[[3-(Bicyclo[2.2.1]hept-2-yloxy)-4-methoxyphenyl]methylene]-5-bromo-1,3-dihydro-1-methyl-[1α,2α(Z),4α]-2H-indol-2-one (Example 47)

3-[[3-(Bicyclo[2.2.1]hept-2-yloxy)-4-methoxyphenyl]methylene]-5-bromo-1,3-dihydro-[1α,2α(Z),4α]-2H-indol-2-one (Ex. 16) (374 mg, 0.85 mmol) and potassium carbonate (177 mg, 1.28 mmol) were combined in 10 ml of acetone under an inert atmosphere. To this orange, heterogeneous mixture, was added 0.08 ml of methyl iodide (1.28 mmol) via syringe. The reaction was heated to 65° for 16 hours. The potassium carbonate was filtered off and washed well with $CH_2Cl_2$. The solvent was removed by rotary evaporation to yield a yellow oil which was purified via flash chromatography (1:1 $Et_2O$/hexane) to provide the desired methylated E isomer (89 mg, 23% yield) as a yellow, fluffy solid: mp 133°–135° (Example 46). Analysis calculated for $C_{24}H_{24}BrNO_3$: C, 63.44; H, 5.32; N, 3.08. Found: C, 63.45; H, 5.22; N, 3.02. The corresponding Z adduct 3-[[3-(bicyclo[2.2.1]hept-2-yloxy)-4-methoxyphenyl]methylene]-5-bromo-1,3-dihydro-1-methyl-[1α,2α(Z),4α]-2H-indol-2-one was also obtained in 32% yield (124 mg) as a yellow solid (Example 47): mp 157°–158°. Analysis calculated for $C_{24}H_{24}BrNO_3$: C, 63.44; H, 5.32; N, 3.08. Found: C, 63.22; H, 5.23; N, 3.08.

EXAMPLES 48–55

Following the method of Example 46 the following products were prepared by reacting the appropriate oxindole indicated below in place of the title compound of Example 16 with methyl iodide. The wavy lines indicate that these compounds can exist as either the E or Z stereoisomer as indicated below.

Example 53 is Example 29. The starting material oxindole for Example 54 is Example 30. The starting material oxindole for Example 55 is Example 63.

EXAMPLE 56

3-[[3-(Bicyclo[2.2.1]hept-2-yloxy)-4-methoxyphenyl]methyl]-1,3-dihydro-2H-indol-2-one. 3-[[3-Bicyclo[2.2.1]hept-2-yloxy)-4-methoxyphenyl]methylene]-1,3-dihydro-[1α,2α (E),4α]-2H-indol-2-one (Example 3, 500 mg, 1.38 mmol) was dissolved in 50 ml of ethyl acetate and 25 ml of tetrahydrofuran, placed in a Parr shaker with 180 mg of 10% palladium on carbon and shaken for 2 hours at 50 psi $H_2$. After filtering the reaction mixture through Celite, the solvent was stripped off and the resulting clear oil was recrystallized with 1:2 $Et_2O$/hexane to provide the title compound (447 mg, 89% yield) as a fine white powder: mp 157°–158°. Analysis calculated for $C_{23}H_{25}NO_3$•¼$H_2O$: C 75.08; H 6.99; N 3.81. Found: C 75.25; H 6.85; N, 3.85. M/z calculated for $C_{23}H_{25}NO_3$; 363.1834. Found 363.18699.

EXAMPLES 57–58

Following the method of Example 56, the following products were prepared by hydrogenating the appropriate oxindole indicated below in place of the title compound of Example 3.

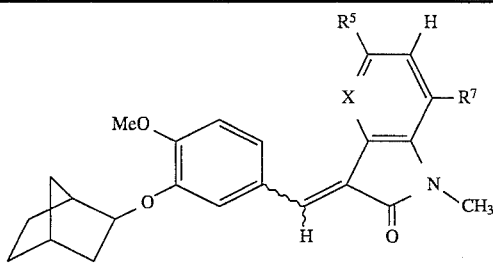

| Ex. | $R^5$ | $R^7$ | X | Stchm | mp (°C.) | MF for Analysis | Anal. | C | H | N | MF for m/z | m/z |
|---|---|---|---|---|---|---|---|---|---|---|---|---|
| 48 | $NO_2$ | H | C—H | E | 124–145 | $C_{24}H_{24}N_2O_5$•½$H_2O$ | Calc: Found: | 67.12 67.09 | 5.87 5.57 | 6.52 6.43 | $C_{24}H_{24}N_2O_5$ | Calc: 420.1685 Found: 420.1699 |
| 49 | $NO_2$ | H | C—H | Z | 215–216 | $C_{24}H_{24}N_2O_5$•½$H_2O$ | Calc: Found: | 67.12 67.26 | 5.87 5.55 | 6.52 6.51 | $C_{24}H_{24}N_2O_5$ | Calc: 420.1685 Found: 420.16823 |
| 50 | $NO_2$ | $NO_2$ | C—H | E | 212–216 | | | | | | $C_{24}H_{23}N_3O_7$ | Calc: 465.1536 Found: 465.1472 |
| 51 | Cl | H | N | E | 178–180 | $C_{23}H_{23}ClN_2O_3$ | Calc: Found: | 67.23 67.30 | 5.64 5.49 | 6.82 6.51 | | |
| 52 | Cl | H | N | Z | 136–138 | $C_{23}H_{23}ClN_2O_3$ | Calc: Found: | 67.23 67.03 | 5.64 5.28 | 6.82 6.66 | | |
| 53 | H | H | N | E | 153.8–155.3 | $C_{23}H_{24}N_2O_3$ | Calc: Found: | 73.38 72.98 | 6.43 6.35 | 7.44 7.40 | | |
| 54 | Me | H | C—H | E | 154–156 | $C_{25}H_{27}NO_3$ | Calc: Found: | 77.10 76.74 | 6.99 7.24 | 3.60 3.42 | | |
| 55 | $OC_5H_9$ | H | C—H | Z | semi-solid | | | | | | $C_{29}H_{33}NO_4$ | Calc: 459.2410 Found: 459.2443 |

The starting material oxindole for Examples 48 and 49 is Example 26. The starting material oxindole for example 50 is Example 27. The starting material oxindole for Examples 51 and 52 is Example 28. The starting material oxindole for

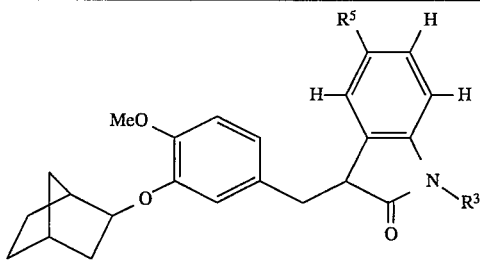

| Ex. | R³ | R⁵ | Catalyst | Solvent | mp (°C.) | MF for Analysis | Anal. | C | H | N | MF for m/z | m/z |
|---|---|---|---|---|---|---|---|---|---|---|---|---|
| 57 | H | OH | 10% Pd/C | EtOAc/ THF | 186–188 | $C_{23}H_{25}NO_4 \cdot \frac{1}{4}H_2O$ | Calc: Found: | 71.95 71.94 | 6.69 6.59 | 3.65 3.62 | $C_{23}H_{25}NO_4$ | Calc: 379.1784 Found: 380.18429 |
| 58 | NO₂ | H | PtO₂ | EtOAc | foam | | | | | | $C_{24}H_{28}N_2O_3$ | Calc: 392.2100 Found: 392.21327 |

EXAMPLE 59 & 60

3-[[3-Bicyclo[2.2.1]hept-2-yloxy)-4-methoxyphenyl]methylene]2,3-dihydro-2-oxo-[1α, 2α(E),4α]-1H-indol-1-carboxylic acid, ethyl ester (Example 59) and 3-[[3-bicyclo[2.2.1]-hept-2-yloxy)-4-methoxyphenyl]methylene]2,3-dihydro-2-oxo-[1α,2α(Z),4α]-1H-indol-1 carboxylic acid, ethyl ester (Example 60)

The title compound of Example 3 (1.0 g, 2.77 mmol), ethyl chloroformate (10.0 ml), and potassium carbonate (770 mg, 5.6 mmol) were combined under an inert atmosphere. The reaction mixture was stirred at room temperature overnight and then at 100° C. for 6 hours. The solvent was then stripped off and the resulting yellow oil was purified via flash chromatography (1:1 ethyl ether/hexane) to provide the E isomer (82.6 mg, 7% yield) as bright yellow crystals (Example 59): m.p. 123°–124° C. Analysis calculated for $C_{26}H_{27}NO_5$C, 72.04; H, 6.28; N, 3.23. Found: C, 71.99; H, 6.20; N, 3.22. The corresponding Z isomer (Example 60) was also obtained in 16% yield: m.p. 60°–70° C. Analysis calculated for $C_{26}H_{27}NO_6$: C, 72.04; H, 6.28; N, 3.23. Found: C, 72.14; H, 6.09; N, 3.18.

EXAMPLE 61

3-[[3-(Bicyclo[2.2.1]hept-2-yloxy)-4-methoxyphenyl]methylene]-5-acetoxy-1,3 -dihydro[1α, 2α,(Z),4α]-2H-indol-2-one The title compound of Example 10 (1.0 g, 2.65 mmol) was combined with 10 ml of 2N NaOH solution and heated to 55° C. To this dark red, heterogeneous mixture was added 0.25 ml of acetic anhydride (2.65 mmol) via syringe. The reaction mixture was stirred at 55° C. for 1 hour. The reaction mixture was then taken up in 200 ml H₂O, adjusted to pH 7.5 with 1N HCl, extracted with 3×150 ml ethyl ether, dried over MgSO₄, filtered, and the solvent stripped off. The resulting yellow-orange oil was purified via flash chromatography (1:1 ethyl ether/hexane) to provide the title compound (57.8 mg, 5% yield) as a yellow-orange powder: m.p. 192°–194° C. M/z calculated for $C_{25}H_{25}NO_5$: 419.1733. Found: 419.1731.

EXAMPLES 62 & 63

3-[[3-(Bicyclo[2.2.1]hept-2-yloxy)-4-methoxyphenyl]methylene]-5-cyclopentyl-1,3-dihydro-[1α,2α,(E),4α]-2H-indol-2-one (Example 62) and 3-[[3-(Bicyclo[2.2.1]hept-2-yloxy)-4-methoxyphenyl]methylene]-5-cyclopentyl-1,3-dihydro-[1α,2α,(Z),4α]-2H-indol-2-one (Example 63)

The title compound of Example 10 (1.0 g, 2.65 mmol) was dissolved in 25 ml of DMF (dimethylformamide) under an inert atmosphere and cooled to 0° C. To this bright orange, homogeneous solution was added NaH (60% dispersion in oil, 225 mg, 5.63 mmol) in one portion. The reaction mixture was stirred for 1 hour at 0° C. and cyclopentyl chloride (0.3 ml, 2.88 mmol) was then added via syringe. The reaction mixture was then stirred at room temperature for 10 hours. The solvent was removed by Kugelrohr distillation and the black residue was taken up in 500 ml of ethyl ether. The resulting solution was washed twice with 300 ml H₂O and once with 300 ml saturated brine solution, and then dried over MgSO₄. The solution was then filtered and the solvent was stripped off. The resulting purple oil was purified via flash chromatography (1:1 ethyl ether/ hexane) to provide the E isomer (53 mg, 5% yield) as a bright red powder (Example 62): m.p. 186°–187° C. Analysis calculated for $C_{28}H_{31}NO_4 \cdot \frac{1}{2}H_2O$: 73.98; H, 7.10; N, 3.08. Found: C, 74.26; H, 6.90; N, 3.06. M/z calculated for $C_{28}H_{31}NO_4$: 445.2253. Found: 445.2258. The corresponding Z isomer (Example 63) was also obtained in 11% yield: m.p. 190°–191° C. Analysis calculated for $C_{28}H_{31}NO_4$: C, 75.48; H, 7.01; N, 3.14. Found: C, 75.39; H, 7.16; N, 2.97. M/z calculated for $C_{28}H_{31}NO_4$: 445.225. Found: 445.2229.

EXAMPLES 64 & 65

3-[[3-Bicyclo[2.2.1]hept-2-yloxy)-4-methoxyphenyl]methylene]-5-cyclopentyl-1,3 -dihydro-1-ethyl-[1α,2α(E),4α]-2H-indol-2-one (Example 64) and 3-[[3-Bicyclo[2.2.1]hept-2-yloxy)-4-methoxyphenyl]methylene]-5-cyclopentyl-1,3-dihydro-1-ethyl-[1α,2α(Z),4α]-2H-indol-2-one (Example 65)

The title compound of Example 11 (1.06 g, 2.61 mmol), cyclopentanol (0.31 ml, 3.42 mmol) and triphenylphosphine (1.028 g, 3.92 mmol) were combined in 50 ml of tetrahydrofuran under an inert atmosphere. To this dark red homogeneous solution was added 0.62 ml of diethylazodicarboxylate (3.94 mmol) via syringe. The reaction mixture was stirred at room temperature for 72 hours. The solvent was then stripped off and the resulting orange oil was purified via flash chromatography (1:1 ethyl ether/hexane) to provide the E isomer (200 mg, 16% yield) as an orange foam (Example 64). Analysis calculated for $C_{30}H_{35}NO_4$: C, 76.08; H, 7.45; N, 2.96. Found: C, 76.32; H, 7.39; N, 2.90. The corresponding Z isomer (Example 65) was also obtained in 66% yield (821 mg) as an orange foam. Analysis calculated for $C_{30}H_{35}NO_4$: C, 76.08; H, 7.45; N, 2.96. Found: C, 76.07; H, 7.50; N, 3.00.

EXAMPLE 66

3-[[3-(Bicyclo[2.2.1]hept-2-yloxy)-4-methoxyphenyl]methylene]-5-bromo-2,3-dihydro-2-oxo-[1α,2α(E),4α]-1H-indole-1-acetic acid, ethyl ester The title compound of Example 16 (287 mg, 0.65 mmol) and ethyl chloroacetate (0.07 ml, 0.77 mmol) were dissolved in 30 ml of DMF (dimethylformamide) under an inert atmosphere. The reaction mixture was cooled to 0° C. whereupon 31.1 mg of NaH (60% dispersion in oil, 0.78 mmol) was added. The reaction mixture was stirred at 0° C. for 20 minutes and then allowed to warm to room temperature. The reaction mixture was poured in 100 ml of $H_2O$, extracted with three 100 ml portions of ethyl ether, dried over $MgSO_4$, filtered, and the solvent stripped off. The remaining DMF was removed via Kugelrohr distillation and the resulting oil was purified via flash chromatography (1:1 ethyl ether/hexane) to provide the title compound (40 mg, 12% yield) as a yellow solid: m.p. 141°–143° C.

EXAMPLES 67–68

Following the method of Example 66, the following products were prepared by reacting ethyl chloroacetate with the appropriate oxindole in place of the title compound of Example 16. The starting material oxindole is known in the literature. The wavy lines indicate that these compounds can exist as either the E or Z stereoisomers, as indicated below.

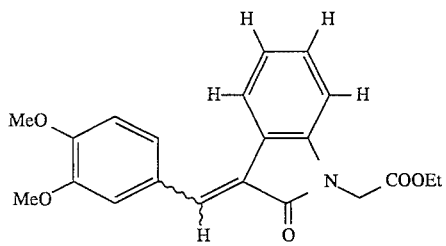

| Ex. | Stchm. | mp (°C.) | MF for Analysis | Anal. | C | H | N |
|---|---|---|---|---|---|---|---|
| 67 | E | 143–144 | $C_{21}H_{21}NO_5$ | Calc: | 68.65 | 5.76 | 3.81 |
|    |   |         |                    | Found: | 68.21 | 5.59 | 3.98 |
| 68 | Z | 148–149 | $C_{21}H_{21}NO_5$ | Calc: | 68.65 | 5.76 | 3.81 |
|    |   |         |                    | Found: | 68.57 | 5.64 | 3.83 |

EXAMPLE 69

3-[[3-(Bicyclo[2.2.1]hept-2-yloxy)-4-methoxyphenyl]methylene]-5-amino-1,3-dihydro-1-methyl-[1α,2α(Z),4α]-2H-indol-2-one The title compound of Example 49 (446 mg, 1.06 mmol) and iron powder (355 mg, 6.36 mmol) were combined in 9 ml of 1:1 ethanol/water and heated to 96° C. under an inert atmosphere. To this yellow, heterogeneous mixture was added 0.03 ml of 12N HCl in 0.29 ml ethanol via syringe. The reaction mixture was stirred at 100° C. for 1 hour, whereupon 1N NaOH solution was added until the pH was equal to 8. The iron was filtered off through a pad of diatomaceous earth (CELITE®). The pad was washed with water and then with ethyl acetate. The two layers were then separated, the organic layer was washed with 100 ml of saturated brine solution, dried over $MgSO_4$, filtered, and stripped to a red oil. This crude oil was purified via flash chromatography (ethyl ether) to provide the title compound (151 mg, 36% yield) as a red powder: m.p. 170°–172° C. M/z calculated for $C_{24}H_{26}N_2O_3$: 390.1943. Found: 390.18906.

PREPARATIONS

PREPARATION A

N-methyl-5-methoxyoxindole 5-methoxy oxindole (450 mg, 2.76 mmol) and potassium carbonate (585 mg, 4.23 mmol) were combined in 45 ml of acetone under an inert atmosphere. To this white, heterogenous mixture was added 0.33 ml of methyl iodide (5.30 mmol) via syringe. The reaction mixture was stirred at room temperature for 10 hours and then at 75° C. for 3 hours. Additional potassium carbonate and methyl iodide were added (290 mg and 0.11 ml, respectively), and the reaction mixture was stirred at 75° C. for 6 more hours. The reaction mixture was then poured into 300 ml of saturated brine solution and extracted with 3×200 ml ether. The combined organic layers were dried over $MgSO_4$, filtered, and stripped to a yellow oil. This was purified via flash chromatography (3:1 ethyl ether/hexane) to provide the title compound (307 mg, 63% yield) as white crystals: m.p. 93°–94° C. M/z calculated for $C_{10}H_{11}NO_2$: 177.0790, Found: 177.08066.

PREPARATIONS B & C

Following the method of Preparation A, the following products were prepared by reacting the appropriate oxindole with methyl iodide. The appropriate oxindoles are known in the literature.

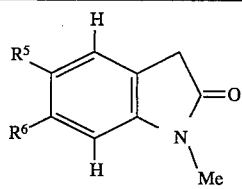

| Prep. | R⁵ | R⁶ | mp (°C.) | To Form Ex. No. | MF for Analysis | Anal. | C | H | N | MF for m/z | m/z |
|---|---|---|---|---|---|---|---|---|---|---|---|
| B | H | OMe | 96–98 | 36, 37 | | | | | | $C_{10}H_{11}NO_2$ | Calc: 177.0790 Found: 177.0781 |
| C | OMe | OMe | 117–118 | 38, 39 | $C_{11}H_{13}NO_3$ | Calc: Found: | 63.76 63.36 | 6.32 6.36 | 6.76 6.52 | $C_{11}H_{13}NO_3$ | Calc: 207.0895 Found: 207.08961 |

PREPARATION D

5-(N,N-dimethylsulfonamidyl)oxindole

To a suspension of $AlCl_3$ (108 g, 0.81 mol) in $CS_2$ (370 ml) was added dimethylsulfamoyl chloride (17.2 ml, 0.16 mol), followed by oxindole (17.6 g, 0.132 mol, ALDRICH). The reaction mixture was heated to reflux for 4.5 hours. The $CS_2$ solution was decanted off, leaving a gummy solid. The solid was scraped into crushed ice and stirred for 30 minutes. The solid was filtered to yield the title compound (9.3 g, 39% yield) as a tan solid: m.p. 208°–215° C.

PREPARATION E

4-Methoxy-3-(4-phenylbutyroxy)benzaldehyde

Following the method of Example 64, the title compound was prepared from 3-hydroxy-4-methoxybenzaldehyde (ALDRICH) and 4-phenyl-1-butanol (Aldrich). M/z calculated for $C_{18}H_{20}O_3$: 284.1412. Found: 284.1435.

PREPARATION F

2-(3-[3-(Bicyclo[2.2.1]hept-2-yloxy)]-4-methoxyphenyl)-2-hydroxyethane 3-(exo-Bicyclo[2.2.1]hept-2-yloxy)-4-methoxybenzaldehyde (as disclosed in WO 87/06576 published Nov. 5, 1987) (7.0 g, 28.4 mmol) was dissolved in 100 ml of tetrahydrofuran under an inert atmosphere and cooled to 0° C., whereupon 10.42 ml of 3.0M methyl magnesium bromide in ethyl ether was added via syringe. The reaction mixture was stirred at 0° C. for 1 hour and then at room temperature for 1 hour. The reaction mixture was slowly poured into a mixture of 500 ml of saturated brine solution and 500 ml of ethyl ether. The layers were separated and the aqueous layer was extracted with two 300 ml portions of ethyl ether. The combined organic layers were dried over $MgSO_4$, filtered and stripped to a yellow oil. This was purified by flash chromatography (2:1 hexane/ethyl ether) to provide the title compound (4.98 g, 67% yield) as a yellow solid: m.p. 60°–61.5° C. Analysis calculated for $C_{16}H_{22}O_3$: C, 73.25; H, 8.45. Found: C, 73.54; H, 8.59. M/z calculated for $C_{16}H_{22}O_3$: 262.1569. Found: 262.1564.

PREPARATION G

Aceto-(3-[3-bicyclo[2.2.1]hept-2-yloxy)]-4-methoxy)phenone

The title compound of Preparation F (4.98 g, 19 mmol) and 27 ml of $H_2O$ were combined and cooled to 0° C. To this yellow suspension was added 2.17 ml of concentrated sulfuric acid. Acetone (103 ml) was then added and the reaction mixture was stirred at 0° C. until the mixture became homogeneous. Finally, 27.1 ml of Jones reagent was added rapidly by syringe, whereupon the reaction mixture was stirred at 0° C. for 15 minutes and room temperature for 1 hour. The reaction mixture was then slowly poured into 500 ml saturated bicarbonate solution and stirred for 15 minutes at room temperature. This mixture was extracted with three 300 ml portions of ethyl ether and once with 300 ml $CH_2Cl_2$. The combined organic layers were dried over $MgSO_4$, filtered, and stripped to a yellow oil. This crude material was recrystallized in 150 ml warm hexane to yield the title compound (4.19 g, 85% yield) as light brown crystals: m.p, 95°–97° C. Analysis calculated for $C_{16}H_{20}O_3$: C, 73.82; H, 7.74. Found: C, 73.73; H, 7.65. M/z calculated for $C_{16}H_{20}O_3$: 260.1412. Found: 260.1404.

I claim:

1. A compound of the formula:

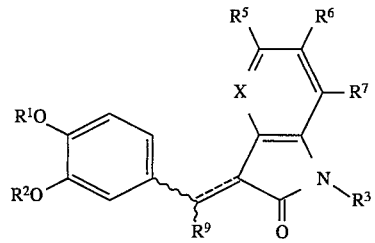

wherein X is N or $CR^4$;

$R^1$ is $(C_1–C_4)$alkyl or phenyl-$(C_1–C_6)$alkyl;

$R^2$ is $(C_1–C_{10})$alkyl, phenyl-$(C_1–C_6)$alkyl, $(C_3–C_7)$ cycloalkyl, or $(C_6–C_{12})$ polycycloalkyl;

or $R^1$ and $R^2$, taken together with the oxygens to which they are attached, represent a methylene or ethylene bridge which forms a 5 or 6 membered ring;

$R^3$ is hydrogen, $(C_1–C_6)$alkyl, $(C_1–C_6)$alkyloxycarbonyl, $(C_1–C_6)$alkyloxy, $(C_1–C_6)$ alkoxycarbonyl-$(C_1–C_6)$alkyl, —$CONR^{10}R^{11}$; or -$(C_1–C_6)$alkyl-$CONR^{10}R^{11}$;

$R^{10}$ and $R^{11}$ are independently selected from hydrogen and $(C_1–C_6)$alkyl, or $R^{10}$ and $R^{11}$, taken together with the nitrogen to which they are attached, form a pyrrolidine or piperidine ring;

$R^4$, $R^5$, $R^6$ and $R^7$ are independently selected from hydrogen, halogen, $(C_1-C_8)$ alkoxy, $(C_3-C_7)$ cycloalkyloxy, hydroxy, $(C_2-C_6)$ acyloxy, nitro, $NR^8R^{12}$, $SO_2NR^8R^{12}$, $(C_1-C_6)$alkyl, $(C_1-C_6)$ alkylcarbonyl, phenyl-$(C_1-C_6)$alkoxy, and $(C_6-C_{12})$ polycycloalkoxy or any combination of $R^4$ and $R^5$, $R^5$ and $R^6$, or $R^6$ and $R^7$ which together form —OCH$_2$O— or —OCH$_2$CH$_2$O—, such that, when taken together with the carbons to which they are attached, they form, respectively, a 5- or 6-membered ring;

$R^8$ and $R^{12}$ are independently selected from hydrogen and $(C_1-C_6)$alkyl, or $R^8$ and $R^{12}$, taken together with the nitrogen to which they are attached, form a pyrrolidine or piperidine ring;

$R^9$ is hydrogen or $(C_1-C_6)$alkyl;

the broken line represents an optional double bond; and the wavy lines indicate that the compounds exist as (E) and/or (Z) stereoisomers when the broken line is a double bond;

with the proviso that (a) if $R^1$ and $R^2$ are both methyl, X is CH, $R^9$ is hydrogen, and the broken line is a double bond, then (i) at least one of $R^3$, $R^5$, $R^6$, and $R^7$ is other than hydrogen; (ii) at least one of $R^5$, $R^6$ and $R^7$ is other than hydrogen or $R^3$ is other than methyl; and (iii) at least one of $R^3$ and $R^7$ is other than hydrogen or at least one of $R^5$ and $R^6$ is other than O—CH$_3$; (b) if $R^3$ is hydrogen, $R^9$ is hydrogen, X is CH, the broken line is a double bond, and $R^1$ and $R^2$ together represent a methylene bridge, then at least one of $R^5$, $R^6$ and $R^7$ is other than hydrogen; and (c) if $R^1$ and $R^2$ are both methyl, X is CH, $R^9$ is hydrogen, and the broken line is a single bond, then at least one of $R^5$ and $R^6$ is other than O—CH$_3$, or $R^7$ is other than hydrogen, or $R^3$ is other than COCH$_3$;

or a pharmaceutically acceptable salt thereof.

2. A compound according to claim 1 wherein:

$R^1$ is methyl or ethyl and $R^2$ is $(C_1-C_6)$alkyl, phenyl-$(C_1-C_6)$alkyl, $(C_3-C_7)$ cycloalkyl, or $(C_6-C_{12})$ polycycloalkyl; or $R^1$ and $R^2$, taken together with the oxygens to which they are attached, represent a methylene or ethylene bridge which forms a 5 or 6 membered ring.

3. A compound according to claim 1 wherein X is CH or N, $R^1$ is methyl, $R^2$ is norbornyl, $R^3$ is hydrogen, methyl, ethyl, —COOC$_2$H$_5$, —CONH$_2$, methoxy or —CH$_2$COOC$_2$H$_5$, $R^6$ is hydrogen, bromo, methoxy or chloro, and $R^5$ is hydrogen, hydroxy, cyclopentyloxy, methoxy, bromo, chloro, amino, or —SO$_2$NH$_2$, or $R^5$ and $R^6$ together form —OCH$_2$O—, $R^7$ is hydrogen, and $R^9$ is hydrogen or methyl.

4. A compound according to claim 1 selected from the group consisting of:

3-[[3-(Bicyclo[2.2.1]hept-2-yloxy)-4-methoxyphenyl]methylene]-1,3-dihydro-[1α,2α(E),4α]-2H-indol-2-one;

3-[[3-(Bicyclo[2.2.1]hept-2-yloxy)-4-methoxyphenyl]methylene]-1,3-dihydro-1-ethyl-[1α,2α(E),4α]-2H-indol-2-one;

3-[[3-(Bicyclo[2.2.1]hept-2-yloxy)-4-methoxyphenyl]methylene]-1,3-dihydro-1-methyl-[1α,2α(Z),4α]-2H-indol-2-one;

3-[[3-(Bicyclo[2.2.1]hept-2-yloxy)-4-methoxyphenyl]methylene]-1,3-dihydro-1-ethyl-[1α,2α(Z),4α]-2H-indol-2-one;

3-[[3-(Bicyclo[2.2.1]hept-2-yloxy)-4-methoxyphenyl]methylene]-6-chloro-1,3-dihydro-1-methoxy-[1α,2α(Z),4α]-2H-indol-2-one;

3-[[3-(Bicyclo[2.2.1]hept-2-yloxy)-4-methoxyphenyl]methylene]-6-chloro-1,3-dihydro-[1α,2α(E),4α]-2H-indol-2-one;

3-[[3-(Bicyclo[2.2.1]hept-2-yloxy)-4-methoxyphenyl]methylene]-5-bromo-1,3-dihydro-[1α,2α(E),4α]-2H-indol-2-one;

3-[[3-(Bicyclo[2.2.1]hept-2-yloxy)-4-methoxyphenyl]methylene]-5-bromo-1,3-dihydro-1-methyl-[1α,2α(E),4α]-2H-indol-2-one;

3-[[3-(Bicyclo[2.2.1]hept-2-yloxy)-4-methoxyphenyl]methylene]-5-chloro-1,3-dihydro-1-methyl-[1α,2α(Z),4α]-2H-indol-2-one;

3-[[3-(Bicyclo[2.2.1]hept-2-yloxy)-4-methoxyphenyl]methylene]-5-cyclopentyloxy-1,3-dihydro-1-ethyl-[1α,2α(E),4α]-2H-indol-2-one;

3-[[3-(Bicyclo[2.2.1]hept-2-yloxy)-4-methoxyphenyl]methylene]-6-methoxy-1,3-dihydro-1-methyl[1α,2α(E),4α]-2H-indol-2-one; and 3-[[3-(Bicyclo[2.2.1]hept-2-yloxy)-4-methoxyphenyl]methylene]-2,3-dihydro-N,N-dimethyl-2-oxo-[1α,2α(E),4α]-1H-indole-5-sulfonamide.

5. A pharmaceutical composition for inhibiting the effects of phosphodiesterase type IV in a mammal, including a human, comprising a phosphodiesterase type IV inhibiting amount of a compound of claim 1, and a pharmaceutically acceptable carrier.

6. A method of inhibiting the effects of phosphodiesterase type IV in a mammal, including a human, comprising administering to said mammal a phosphodiesterase type IV inhibiting amount of a compound of claim 1.

7. A pharmaceutical composition for treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising an amount of a compound of claim 1, effective in inhibiting the action of phosphodiesterase type IV, and a pharmaceutically acceptable carrier.

8. A pharmaceutical composition for treating a disorder in a mammal, including a human, the treatment of which is effected or facilitated by blocking the action of phosphodiesterase type IV, comprising an amount of a compound of claim 1, effective in treating such disorder, and a pharmaceutically acceptable carrier.

9. A method of treating a disorder in a mammal, including a human, the treatment of which is effected or facilitated by blocking the action of phosphodiesterase type IV, comprising administering to said mammal an amount of a compound of claim 1, effective in treating such a disorder.

* * * * *